US006436407B1

(12) United States Patent
Clements et al.

(10) Patent No.: US 6,436,407 B1

(45) Date of Patent: Aug. 20, 2002

(54) MUTANT ENTEROTOXIN EFFECTIVE AS A NON-TOXIC ADJUVANT

(75) Inventors: John D. Clements, New Orleans, LA (US); Bonny L. Dickinson, Boston, MA (US)

(73) Assignee: The Administrators of the Tulane Educational Fund, New Orleans, LA (US)

(*) Notice: Subject to any disclaimer, the term of this patent is extended or adjusted under 35 U.S.C. 154(b) by 0 days.

(21) Appl. No.: 09/368,618

(22) Filed: Aug. 4, 1999

Related U.S. Application Data

(63) Continuation of application No. 08/790,691, filed on Jan. 29, 1997, now abandoned, which is a continuation-in-part of application No. 08/296,848, filed on Aug. 26, 1994, now Pat. No. 6,019,982.

(51) Int. Cl.[7] ........................ A61K 39/21; A61K 39/02; A61K 45/00; A61K 39/00; A61K 1/00

(52) U.S. Cl. ............................... 424/208.1; 424/236.1; 424/234.1; 424/235.1; 424/200.1; 424/184.1; 424/278.1; 424/282.1; 530/350; 530/825

(58) Field of Search ........................... 424/208.1, 236.1, 424/184.1, 200.1, 234.1, 278.1, 235.1, 257.1, 241.1, 832, 282.1; 530/825, 350

(56) References Cited

U.S. PATENT DOCUMENTS 5,182,109 A 1/1993 Tamura et al.

FOREIGN PATENT DOCUMENTS

| | | |
|---|---|---|
| GB | 2217600 A | 1/1989 |
| WO | WO 92/19265 | 11/1992 |
| WO | WO 93/13202 | 7/1993 |
| WO | WO 95/17211 | 6/1995 |

OTHER PUBLICATIONS

DeSousa et al. Common Medical Abbreviations, Delmar Publishers, Washington, 1994, pp. 10 and 152.*

Douce et al., 1995, "Mutants of *Escherichia coli* heat–labile toxin lacking ADP–ribosyltranferase activity act as non-toxic, mucosal adjuvants", Proc Natl Acad Sci 92:1644–1648.

Backstrom et al., 1994, Gene 149:211–217.

Fox, 1994, Bio/Technology 12:128.

Grant et al., 1994, Infection and Immunity 62(10):4270–78.

Häse et al., 1994, "Construction and characterization of recombinant *Vibrio cholerae*strains producing inactive cholera toxin analogs",Infect. Immun. 62(8):3051–3057.

Holmgren et al., 1994, *Am J. Trop. Med Hyg* 50:42–54.

McGhee et al., 1994, "Vaccines for mucosal immunity: Unique delivery system and immune response analyses for TH1/TH2 cells and IgE/IgA B cells", Mucosal Immunology Update, Spring 1994, Raven Press, New York p. 21.

Pizza et al., 1994, Molecular Microbiology, 14(1):51–60.

Cohen, 1993 (Nov. 12), Science 262:980.

Conner et al., 1993, "Rotavirus vaccineadministered parenterally induces protective immunity", J. Virol. 67(11):6633–6641.

Gould–Fogerite and MAnnino, 1993, In: Liposome Technology, Second Edition, vol. III, Gregoriadis (ed.), CRC Press, Boca Raton pp. 261–276.

Holmgren et al., 1993, *Vaccine 11(12)*:1179–1186.

Moss et al., 1993, "Interaction of ADP–ribosylation factor with *Escherichia coli* enterotoxin that contains an inactivating lysine 112 substitution", J. Biol. Chem. 268(9):6383–6387.

Santiago et al., 1993, "Oral immunization of rats with proteinoid microspheres encapsulating influenza virus antigens", Pharmaceutical Research 10(8):1243–1247.

Cardenas and Clements, 1992, "Oral immunization using live attenuated *Salmonella* spp. as carriers of foreign antigens", Clin. Microbiol. Rev. 5(3):328–342.

Clements et al., 1992, In: Recombinant DNA vaccines: Rationale and Strategy, Isaacson (ed.), Marcel Decker, New York pp.293–321.

Good, Michael F., 1992, Immunology Today, 13(4):126–130.

Lycke et al., 1992, "The adjuvant effect of *Vibrio cholerae and Escherichia coli* heat–labile enterotoxins is linked to their ADP–ribosyltransferase activity", Eur. J. Immunol. 22:2277–2281.

Burnette et al., 1991, "Site–specific mutagenesis of the catalytic subunit of cholera toxin: Substituting lysine for arginine 7 causes loss of activity", Infection and Immunity 59(11):4266–4270.

Garcon and Six , 1991, "Universal vaccine carrier: Liposomes that provide T–dependent help to weak antigens", J. Immunol. 146:3697–3702.

Lobet et al., 1991, "Effect of site–directed mutagenic alterations on ADP–ribosyltransferase activity of the A subunit of *Escherichia coli* heat–labile enterotoxin", Infection and Immunity 59(9):2870–2879.

Mowat and Donachie, 1991 "ISCOMS —a novel strategy for mucosal immunization", Immunol. Today 12(11):383–385.

Arai et al., 1990, "Cytokines: Coordinators of immune and inflammatory responses", Annu. Rev. Biochem. 59:783–836.

Clements and Cardenas, 1990, "Vaccines against enterotoxigenic bacterial pathogens based on hybrid *Salmonella* that express heterologous antigens", Res. Microbiol. 141:981–993.

(List continued on next page.)

*Primary Examiner*—S. Devi

(74) *Attorney, Agent, or Firm*—Pennie & Edmonds LLP

(57) ABSTRACT

Methods and compositions are provided herein for the use of a novel mutant form of *E. coli* heat-labile enterotoxin which has lost its toxicity but has retained its immunologic activity. This enterotoxin is used in combination with an unrelated antigen to achieve an increased immune response to said antigen when administered as part of a vaccine preparation.

14 Claims, 9 Drawing Sheets

OTHER PUBLICATIONS

Loosmore et al., 1990, Infection and Immunity 58(11):3653–62.

Williams et al., 1990, Journal of Biological Chemicstry, 265(33):20673–7.

Brandtzaeg, 1989, "Overview of the mucosal immune system", Curr. Top. Microbiol. Immunol. 146:13–25.

Elson, 1989, "Cholera toxin and its subunits as potential oral adjuvants", Curr. Topics Microbiol. Immunol. 146:29–33.

Clements et al., 1988, "Cross–protection by B subunit–whole cell cholera vaccine against diarrhea associated with heat–labile toxin–producing enterotoxigenic *Escherichia coli*: Results of a large–scale field trial", J. Infect. Dis. 158(2):372–377.

Clements et al., 1988, "Adjuvant activity of *Escherichia coli* heat–labile enterotoxin and effect on the induction of oral tolerance in mice to unrelated protein antigens", Vaccine 6:269–277.

Clements et al., 1988, "*Escherichia coli* heat labile entertoxin possesses adjuvant activity and prevents the induction of oral tolerance in mice to unrelated protein antigens", Abstract No. B–91, 88th Ann. Meet. Am. Soc. Microbiol.

Liang et al., 1988, "Oral administration of cholera toxin-Sendai virus conjugate potentiates gut and respiratory immunity against Sendai virus", J. Immunol. 141(5):1495–1501.

Okamoto et al., 1988, "Effect of substitution of glycine for arginine at position 146 of the A1 subunit on biological activity of *Escherichia coli* heat–labile enterotoxin", J Bacteriol 170(5):2208–2211.

Alving et al., 1986, "Effectiveness of liposomes as potential carriers of vaccines: Applications to cholera toxin and human malaria sporozoite antigen", Vaccine 4:166–172.

Cebra et al., 1986, In: Vaccines 86, Brown et al. (eds.), Cold Spring HArbor Laboratory, New York pp. 129–133.

Lai et al., 1986, "Advances in Enzymology and Related Areas of Molecular Biology", 58:99–140.

Lycke and Holmgren, 1986, "Strong adjuvant properties of cholera toxin on gut mucosal immune responses to orally presented antigens", Immunology 59:301–308.

Owen et al., 1986, "M cell transport og *Vibrio cholerae* from the intestinal lumen into Peyer's patches: A mechanism for antigen sampling and for microbial transepithelial migration", J. Infect. Dis. 153(6):1108–1118.

Strober and Jacobs, 1985, In: Advances in host defense mechanisms, vol. 4., Mucosal Immunity, Gallin and Fauci (eds.), Raven Press, New York, pp. 1–30.

* cited by examiner

```
                    SEQUENCE LISTING


(1) GENERAL INFORMATION:

   (iii) NUMBER OF SEQUENCES: 5


(2) INFORMATION FOR SEQ ID NO:1:

     (i) SEQUENCE CHARACTERISTICS:
          (A) LENGTH: 45 base pairs
          (B) TYPE: nucleic acid
          (C) STRANDEDNESS: double
          (D) TOPOLOGY: unknown

    (ii) MOLECULE TYPE: DNA

    (xi) SEQUENCE DESCRIPTION: SEQ ID NO:1:

GGTTGTGGAG ATTCATCAAG AACAATTACA GGTGATACTT GTAAT                     45


(2) INFORMATION FOR SEQ ID NO:2:

     (i) SEQUENCE CHARACTERISTICS:
          (A) LENGTH: 15 amino acids
          (B) TYPE: amino acid
          (D) TOPOLOGY: linear

    (ii) MOLECULE TYPE: protein

    (xi) SEQUENCE DESCRIPTION: SEQ ID NO:2:

Gly Cys Gly Asp Ser Ser Arg Thr Ile Thr Gly Asp Thr Cys Asn
  1               5                  10                  15


(2) INFORMATION FOR SEQ ID NO:3:

     (i) SEQUENCE CHARACTERISTICS:
          (A) LENGTH: 18 base pairs
          (B) TYPE: nucleic acid
          (C) STRANDEDNESS: double
          (D) TOPOLOGY: unknown
```

-continued

```
    (ii) MOLECULE TYPE: DNA

    (xi) SEQUENCE DESCRIPTION: SEQ ID NO:3:

TCATCAGGAA CAATTACA                                                  18


(2) INFORMATION FOR SEQ ID NO:4:

     (i) SEQUENCE CHARACTERISTICS:
          (A) LENGTH: 45 base pairs
          (B) TYPE: nucleic acid
          (C) STRANDEDNESS: double
          (D) TOPOLOGY: unknown

    (ii) MOLECULE TYPE: DNA

    (xi) SEQUENCE DESCRIPTION: SEQ ID NO:4:

GGTTGTGGAG ATTCATCAGG AACAATTACA GGTGATACTT GTAAT                    45


(2) INFORMATION FOR SEQ ID NO:5:

     (i) SEQUENCE CHARACTERISTICS:
          (A) LENGTH: 15 amino acids
          (B) TYPE: amino acid
          (D) TOPOLOGY: linear

    (ii) MOLECULE TYPE: protein

    (xi) SEQUENCE DESCRIPTION: SEQ ID NO:5:

Gly Cys Gly Asp Ser Ser Gly Thr Ile Thr Gly Asp Thr Cys Asn
  1               5                  10                  15
```

MUTANT ENTEROTOXIN EFFECTIVE AS A NON-TOXIC ADJUVANT

This application is a continuation of application Ser. No. 08/790,691 filed Jan. 29, 1997, currently abandoned, which in turn is a continuation-in-part of application Ser. No. 08/296,848 filed Aug. 26, 1994 currently U.S. Pat. No. 6,019,982.

The research described in this specification was supported in part by the United States Navy, Grant Number N00014-83-K-0192. The government has certain rights in the invention.

1. FIELD OF THE INVENTION

The present invention is directed towards a hgenetically distinct mutant of *E. coli* heat-labile enterotoxin (LT) and its use as an adjuvant to induce mucosal and serum antibodies and cell mediated immune responses. Specifically, the mutant LT is modified by a single amino acid substitution that reduces its inherent toxicity but leaves intact the adjuvant properties of the molecule.

2. BACKGROUND OF THE INVENTION

Microbial pathogens can infect a host by one of several mechanisms. They may enter through a break in the integument induced by trauma, they may be introduced by vector transmission, or they may interact with a mucosal surface. The majority of human pathogens initiate disease by the last mechanism, i.e., following interaction with mucosal surfaces. Bacterial and viral pathogens that act through this mechanism first make contact with the mucosal surface where they may attach and then colonize, or be taken up by specialized absorptive cells (M cells) in the epithelium that overlay Peyer's patches and other lymphoid follicles [Bockman and Cooper, 1973, Am. J. Anat. 136:455–477; Owen et al., 1986, J. Infect. Dis. 153:1108–1118]. Organisms that enter the lymphoid tissues may be readily killed within the lymphoid follicles, thereby provoking a potentially protective immunological response as antigens are delivered to immune cells within the follicles (e.g., *Vibrio cholerae*). Alternatively, pathogenic organisms capable of surviving local defense mechanisms may spread from the follicles and subsequently cause local or systemic disease (i.e., Salmonella spp., poliovirus, rotavirus in immunocompromised hosts).

Secretory IgA (sIgA) antibodies directed against specific virulence determinants of infecting organisms play an important role in overall mucosal immunity [Cebra et al., 1986, In: Vaccines 86, Brown et al. (ed.), Cold Spring Harbor Laboratory, New York. p.p. 129–133]. In many cases, it is possible to prevent the initial infection of mucosal surfaces by stimulating production of mucosal sIgA levels directed against relevant virulence determinants of an infecting organism. Secretory IgA may prevent the initial interaction of the pathogen with the mucosal surface by blocking attachment and/or colonization, neutralizing surface acting toxins, or preventing invasion of the host cells. While extensive research has been conducted to determine the role of cell mediated immunity and serum antibody in protection against infectious agents, less is known about the regulation, induction, and secretion of sIgA. Parenterally administered inactivated whole-cell and whole-virus preparations are effective at eliciting protective serum IgG and delayed type hypersensitivity reactions against organisms that have a significant serum phase in their pathogenesis (i.e., *Salmonella typhi,* Hepatitis B). However, parenteral vaccines are not effective at eliciting mucosal sIgA responses and are ineffective against bacteria that interact with mucosal surfaces and do not invade (e.g., *Vibrio cholerae*). There is, however, recent evidence that parenterally administered vaccines may be effective against at least one virus, rotavirus, that interacts primarily with mucosal surfaces [Conner et al., 1993, J. Virol. 67:6633–6641]. Protection is presumed to result from transudation of antigen specific IgG onto mucosal surfaces for virus neutralization. Therefore, mechanisms that stimulate both serum and mucosal antibodies and cell mediated immunity are important for effective vaccines.

Mucosal immunization can be effective for induction of specific sIgA responses if the antigens are presented to the T and B lymphocytes and accessory cells contained within the Peyer's patches where preferential IgA B-cell development is initiated. The Peyer's patches contain helper T (TH)-cells that mediate B-cell isotype switching directly from IgM cells to IgA B-cells. The patches also contain T-cells that initiate terminal B-cell differentiation. The primed B-cells then migrate to the mesenteric lymph nodes and undergo differentiation, enter the thoracic duct, then the general circulation, and subsequently seed all of the secretory tissues of the body, including the lamina propria of the gut and respiratory tract. IgA is then produced by the mature plasma cells, complexed with membrane-bound Secretory Component, and transported onto the mucosal surface where it is available to interact with invading pathogens [Strober and Jacobs, 1985, In: Advances in host defense mechanisms. Vol. 4. Mucosal Immunity, Gallin and Fauci (ed.), Raven Press, New York. p.p. 1–30; Tomasi and Plaut, 1985, In: Advances in host defense mechanisms. Vol. 4. Mucosal Immunity, Gallin and Fauci (ed.), Raven Press, New York. p.p. 31–61]. The existence of this common mucosal immune system explains in part the potential of live attenuated vaccines and mucosal immunization for protection against pathogenic organisms that initiate infection by first interacting with mucosal surfaces.

A number of strategies have been developed for mucosal immunization, including the use of attenuated mutants of bacteria (i.e., Salmonella spp.) as carriers of heterologous antigens [Cárdenas and Clements, 1992, Clin. Microbiol. Rev. 5:328–342; Clements et al., 1992, In: Recombinant DNA Vaccines: Rationale and Strategy, Isaacson (ed.), Marcel Decker, New York. p.p. 293–321; Clements and Cárdenas, 1990, Res. Microbiol. 141:981–993; Clements and El-Morshidy, 1984, Infect. Immun. 46:564–569], encapsulation of antigens into microspheres composed of poly-DL-lactide-glycolide (PGL), protein-like polymers—proteinoids [Santiago et al., 1993, Pharmaceutical Research 10:1243–1247], gelatin capsules, different formulations of liposomes [Alving et al., 1986, Vaccine 4:166–172; Garcon and Six, 1993, J. Immunol. 146:3697–3702; Gould-Fogerite and Mannino, 1993, In: Liposome Technology 2nd Edition. Vol. III, Gregoriadis (ed.)], adsorption onto nanoparticles, use of lipophilic immune stimulating complexes (ISCOMS) [Mowat and Donachie, 1991, Immunology Today 12:383–385], and addition of bacterial products with known adjuvant properties [Clements et al., 1988, Vaccine 6:269–277; Elson, 1989, Immunology Today 146:29–33; Lycke and Holmgren, 1986, Immunology 59:301–308; Lycke et al., 1992, Eur. J. Immunol. 22:2277–2281]. The two bacterial products with the greatest potential to function as mucosal adjuvants are cholera toxin (CT), produced by various strains of *V. cholerae,* and the heat-labile enterotoxin (LT) produced by some enterotoxigenic strains of *Escherichia coli.* Although LT and CT have many features in common, these are clearly distinct molecules with biochemical and immunologic differences which make them unique.

The extensive diarrhea of cholera is the result of a potent exo-enterotoxin which causes the activation of adenylate cyclase and a subsequent increase in intracellular levels of cyclic 3'-,5'-adenosine monophosphate (cAMP). The cholera enterotoxin (CT) is an 84,000 dalton polymeric protein composed of two major, non-covalently associated, immunologically distinct regions or domains ("cholera-A" and "cholera-B") [Finkelstein and LoSpalluto, 1969, J. Exp. Med. 130: 185–202]. Of these, the 56,000 dalton region, or choleragenoid, is responsible for binding of the toxin to the host cell membrane receptor, $G_{M1}$ (galactosyl-N-acetylgalactosaminyl-(sialyl)-galactosyl-glucosyl ceramide), which is found on the surface of essentially all eukaryotic cells. Choleragenoid is composed of five non-covalently associated monomers, while the A region (27,000 daltons) is responsible for the diverse biological effects of the toxin.

The relationship of the two subunits of CT with respect to the immunologic properties of the molecule has been a source of considerable debate. On the one hand, CT is an excellent immunogen that provokes the development of both serum and mucosal antitoxin antibody responses when delivered mucosally. This finding is not new in that cholera patients are known to develop rises in titers of antitoxin antibodies during convalescence from clinical cholera [Finkelstein, 1975, Curr. Top. Microbiol. Immunol. 69: 137–196]. One key finding of those investigating the nature of this response was the observation that CT, unlike most other protein antigens, is not subject to the phenomenon known as oral tolerance [Elson and Ealding, 1984, J. Immunol. 133: 2892–2897; Elson and Ealding, 1984, J. Immunol. 132: 2736–2741). This was also found to be true when just the B-subunit was fed to mice, an observation substantiated by the cholera vaccine field trials in Bangladesh in which oral immunization with B-subunit combined with killed whole cells gave rise to mucosal as well as systemic antitoxin antibody responses [Svennerholm et al., 1984, J. Infect. Dis. 149: 884–893].

In addition to being a potent mucosal immunogen, CT has a number of other reported immunologic properties. As indicated above, Elson and Ealding [Elson and Ealding, 1984, J. Immunol. 133: 2892–2897] observed that orally administered CT is not subject to oral tolerance. Moreover, simultaneous oral administration of CT with a soluble protein antigen, keyhole limpet hemocyanin (KLH), resulted in the development of secretory IgA responses against both CT and KLH and also abrogated the induction of oral tolerance against KLH. These findings were subsequently confirmed and extended by Lycke and Holmgren [Lycke and Holmgren, 1986, Immunology 59:301–308]. The confusion arises when one attempts to define the role of the A and B subunits of CT with respect to the adjuvant properties of the molecule. The following observations, as summarized by Elson [Elson, 1989, Immunology Today 146:29–33], are the basis for that confusion:

CT is not subject to oral tolerance [Elson and Ealding, 1984, J. Immunol. 133: 2892–2897].

CT-B is not subject to oral tolerance [Elson and Ealding, 1984, J. Immunol. 133: 2892–2897].

CT can prevent the induction of tolerance against other antigens with which it is simultaneously delivered and also serve as an adjuvant for those antigens [Elson and Ealding, 1984, J. Immunol. 133: 2892–2897; Lycke and Holmgren, 1986, Immunology 59:301–308].

CT can act as an adjuvant for CT-B [Elson and Ealding, 1984, J. Immunol. 133: 2892–2897].

Heat aggregated CT has little toxicity but is a potent oral immunogen [Pierce et al., 1983, Infect. Immun. 40: 1112–1118].

CT-B can serve as an immunologic "carrier" in a traditional hapten-carrier configuration [Cebra et al., 1986, In: Vaccines 86, Brown et al. (ed.), Cold Spring Harbor Laboratory, New York. p.p. 129–133; McKenzie and Halsey, 1984, J. Immunol. 133: 1818–1824].

A number of researchers have concluded from these findings that the B-subunit must possess some inherent adjuvant activity. The findings of Cebra et al. [Cebra et al., 1986, In: Vaccines 86, Brown et al. (ed.), Cold Spring Harbor Laboratory, New York. p.p. 129–133], Lycke and Holmgren [Lycke and Holmgren, 1986, Immunology 59:301–308], and Liang et al. [Liang et al., 1988, J. Immunol. 141: 1495–1501] would argue against that conclusion. Cebra et al. [Cebra et al., 1986, In: Vaccines 86, Brown et al. (ed.), Cold Spring Harbor Laboratory, New York. p.p. 129–133] demonstrated that purified CT-B was effective at raising the frequency of specific anti-cholera toxin B-cells in Peyer's patches when given intraduodenally but, in contrast to CT, did not result in significant numbers of IgA committed B-cells. Lycke and Holmgren [Lycke and Holmgren, 1986, Immunology 59:301–308] compared CT and CT-B for the ability to enhance the gut mucosal immune response to KLH by measuring immunoglobulin secreting cells in the lamina propria of orally immunized mice. They found no increase in anti-KLH producing cells in response to any dose of B-subunit tested in their system. Finally, Liang et al. [Liang et al., 1988, J. Immunol. 141: 1495–1501] found no adjuvant effect when CT-B was administered orally in conjunction with inactivated Sendai virus.

Where adjuvant activity has been observed for isolated B-subunit, it has typically been for one of two reasons. First, a traditional method of preparing B-subunit has been to subject holotoxin to dissociation chromatography by gel filtration in the presence of a dissociating agent (i.e., guanidine HCl or formic acid). The isolated subunits are then pooled and the dissociating agent removed. B-subunit prepared by this technique is invariably contaminated with trace amounts of A-subunit such that upon renaturation a small amount of holotoxin is reconstituted. The second reason has to do with the definition of an immunologic carrier. Like many other soluble proteins, B-subunit can serve as an immunologic vehicle for presentation of antigens to the immune system. If those antigens are sufficiently small as to be poorly immunogenic they can be made immunogenic in a traditional hapten-carrier configuration. Likewise, there is a "theoretical" immune enhancement associated with B-subunit, especially for oral presentation, in that B-subunit binds to the surface of epithelial cells and may immobilize an attached antigen for processing by the gut associated lymphoid tissues. However, any potential advantage to this mechanism of antigen stabilization may be offset by the distribution of the antigen across non-immunologically relevant tissues, i.e., the surface of mucosal epithelial cells. In context of the mucosal responsiveness, the immunologically relevant sites for initiation of an immune response are the Peyer's patches, especially for antigen-specific T cell-dependent B cell activation [Strober and Jacobs, 1985, In: Advances in host defense mechanisms. Vol. 4. Mucosal Immunity, Gallin and Fauci (ed.), Raven Press, New York. p.p. 1–30; Tomasi and Plaut, 1985, In: Advances in host defense mechanisms. Vol. 4. Mucosal Immunity, Gallin and Fauci (ed.), Raven Press, New York. p.p. 31–61; Brandtzaeg, 1989, Curr. Top. Microbiol. Immunol. 146: 13–25]. Thus, the events up to isotype switching from IgM cells to IgA B-cells occurs in the Peyer's patches. Antigens localized on the epithelial cell surface may contribute to antigen induced B cell proliferation in that the class II positive epithelial cells may act as antigen presenting cells for T cell activation at the secretory site, thereby increasing cytokine production, terminal B cell differentiation, increased expression of secretory component, and increased external transport of antigen specific IgA [Tomasi, T. B., and A. G. Plaut. 1985, In: Advances in host defense mechanisms. Vol. 4. Mucosal Immunity, Gallin and Fauci (ed.), Raven Press, New York. p.p. 31–61]. The relationships of these events have not been clearly defined for B-subunit as a carrier of other antigens and use of the term "adjuvant" would seem inappropriate for such an effect.

It is clear that the adjuvant property of the molecule resides in the holotoxin in which B-subunit is required for receptor recognition and to facilitate penetration of the A-subunit into the cell. The A-subunit is also required for adjuvant activity, presumably as a function of its ADP-ribosylating enzymatic activity and ability to increase intracellular levels of cAMP (see below). The B-subunit alone may act as a carrier of other antigens in that when conjugated to those antigens they can be immobilized for processing by the mucosal associated lymphoid tissues.

Although LT and CT have many features in common, these are clearly distinct molecules with biochemical and immunologic differences which make them unique, including a 20% difference in nucleotide and amino acid sequence homology [Dallas and Falkow, 1980, Nature 288: 499–501]. The two toxins have the same subunit number and arrangement, same biological mechanism of action, and the same specific activity in many in vitro assays (Clements and Finkelstein, 1979, Infect. Immun. 24:760–769; Clements et al., 1980, Infect. Immun. 24: 91–97].

There are, however, significant differences between these molecules that influence not only their enterotoxic properties, but also their ability to function as adjuvants. To begin with, unlike CT produced by *V. cholerae,* LT remains cell associated and is only released from *E. coli* during cell lysis [Clements and Finkelstein, 1979, Infect. Immun. 24:760–769]. CT is secreted from the vibrio as soon as it is synthesized and can be readily identified in, and purified from, culture supernatants. Consequently, in contrast to CT, LT is not fully biologically active when first isolated from the cell. Consistent with the A-B model for bacterial toxins, LT requires proteolysis and disulfide reduction to be fully active. In the absence of proteolytic processing, the enzymatically active Al moiety is unable to dissociate from the $A_2$ component and cannot reach its target substrate (adenylate cyclase) on the basolateral surface of the intestinal epithelial cell. This is also true for CT, but proteases in the culture supernatant, to which the toxin is exposed during purification, perform the proteolysis. Since LT is not fully biologically active, it is difficult to identify during purification using in vitro biological assays such as the Y-1 adrenal cell assay or permeability factor assay.

The result of this difference in biological activity between LT and CT can be demonstrated as a difference in threshold toxicity between these molecules. For example, in in vitro tests such as cultured Y-1 mouse adrenal tumor cells, there is an approximately 3-log difference in the biological activity of un-nicked LT and CT. In vivo, CT induces detectable net fluid secretion in the rabbit ligated ileal loops at a dose of 0.1 $\mu$g while LT induces net secretion in this same model at a dose of 5 $\mu$g. Significantly, when LT is exposed to proteolytic enzymes with trypsin-like specificity, the molecule becomes indistinguishable from CT in any biologic assay system. This was demonstrated clearly by Clements and Finkelstein [Clements and Finkelstein, 1979, Infect. Immun. 24:760–769].

In addition to the above reported differences, LT has an unusual affinity for carbohydrate containing matrices. Specifically, LT, with a molecular weight of 90,000, elutes from Sephadex columns (glucose) with an apparent molecular weight of 45,000 and from Agarose columns (galactose) with an apparent molecular weight of 0. That is, it binds to galactose containing matrices and can be eluted from those matrices in pure form by application of galactose. LT binds not only to agarose in columns used for purification, but more importantly, to other biological molecules containing galactose, including glycoproteins and lipopolysaccharides. This lectin-like binding property of LT results in a broader receptor distribution on mammalian cells for LT than for CT which binds only to $G_{M1}$. This may account in part for the reported differences in the abilities of these two molecules to induce different helper T lymphocyte responses [McGhee et al., 1994, Mucosal Immunology Update, Spring 1994, Raven Press, New York. p. 21].

In these studies reported by McGhee et al. [McGhee et al., 1994, Mucosal Immunology Update, Spring 1994, Raven Press, New York. p. 21], it was shown that oral immunization of mice with vaccines such as tetanus toxoid (TT) with CT as a mucosal adjuvant selectively induces $T_H2$ type cells in Peyer's patches and spleens as manifested by TH cells which produce IL-4 and IL-5, but not IL-2 or INF-gamma. [For a more complete review of the cytokine network see Arai et al., 1990, Ann. Rev. Biochem. 59:783–836] Importantly, when CT was used as a mucosal adjuvant it also enhanced antigen-specific IgE responses in addition to the IgA response. Such enhancement of IgE responses seriously compromises the safety of CT as a mucosal adjuvant due to the prospect of inducing immediate-type hypersensitivity reactions. In contrast, LT induces both $T_H1$ and $T_H2$ cells and predominantly antigen-specific IgA responses without IgE responses when used as an orally administered mucosal adjuvant.

The two molecules also have many immunologic differences, as demonstrated by immunodiffusion studies [Clements and Finkelstein, 1978, Infect. Immun. 21: 1036–1039; Clements and Finkelstein, 1978, Infect. Immun. 22: 709–713], in vitro neutralization studies, and the partial protection against LT associated *E. coli* diarrhea in volunteers receiving B-subunit whole cell cholera vaccine [Clemens et al., 1988, J. Infect. Dis. 158: 372–377].

Taken together, these findings demonstrate that LT and CT are unique molecules, despite their apparent similarities and that LT is a practical mucosal adjuvant while CT is not.

The demonstration of the adjuvant properties of LT grew out of an investigation of the influence of LT on the development of tolerance to orally administered antigens by one of the present inventors. It was not clear whether or not LT would also influence the induction of oral tolerance or exhibit the adjuvant effects demonstrated for CT, given the observed differences between the two molecules. Consequently, the present inventors examined a number of parameters, including the effect of LT on oral tolerance to ovalbumin (OVA) and the role of the two subunits of LT in the observed response, the effect of varying the timing and route of delivery of LT, the effect of prior exposure to OVA on the ability of LT to influence tolerance to OVA, the use of LT as an adjuvant with two unrelated antigens, and the effect of route of immunization on anti-OVA responses. The results obtained from these studies [Clements et al., 1988, Vaccine 6:269–277; Clements et al., 1988, Abstract No. B91, 88th Ann. Meet. Am. Soc. Microbiol.] are summarized below:

1. Simultaneous administration of LT with OVA was shown to prevent the induction of tolerance to OVA and to increase the serum anti-OVA IgG response 30 to 90 fold over OVA primed and PBS primed animals, respectively. This effect was determined to be a function of the enzymatically active A-subunit of the toxin since the B-subunit alone was unable to influence tolerance induction.
2. Animals fed LT with OVA after an initial OVA prime developed a significantly lower serum IgG and mucosal. IgA anti-OVA response than those fed LT with OVA in the initial immunization, indicating that prior exposure to the antigen reduces the effectiveness of LT to influence tolerance and its ability to act as an adjuvant. LT was not able to abrogate tolerance once it had been established. This was also found to be true for CT when animals were pre-immunized with OVA prior to oral ovalbumin plus CT and offers some insight into the beneficial observation that antibody responses to nontarget dietary antigens are not increased when these adjuvants are used.
3. Serum IgG and mucosal IgA responses in animals receiving LT on only a single occasion, that being upon first exposure to antigen, were equivalent to responses after three OVA/LT primes, indicating that commitment to responsiveness occurs early and upon first exposure to antigen. It was also demonstrated that the direction of the response to either predominantly serum IgG or mucosal IgA can be controlled. by whether or not a parenteral booster dose is administered.
4. Simultaneous administration of LT with two soluble protein antigens results in development of serum and mucosal antibodies against both antigens if the animal has no prior immunologic experience with either. This was an important finding since one possible application of LT as an adjuvant would be for the development of mucosal antibodies against complex antigens, such as killed bacteria or viruses, where the ability to respond to multiple antigens would be important.

Studies by Tamura et al., [Tamura et al., U.S. Pat. No. 5,182,109] demonstrated that LT and/or CT administered intranasally (i.n.) enhanced the antibody titer against a co-administered antigen. However, nowhere in Tamura et al. is it taught that these toxins can induce a protective immune response when administered orally.

Clearly, LT has significant immunoregulatory potential, both as a means of preventing the induction of tolerance to specific antigens and as an adjuvant for mucosally administered antigens and it elicits the production of both serum IgG and mucosal IgA against antigens with which it is delivered. This raises the possibility of an effective immunization program against a variety of pathogens involving the mucosal administration of killed or attenuated agents or relevant virulence determinants of specific agents. However, the fact that this "toxin" can stimulate a net lumenal secretory response when proteolytically cleaved, as by gut proteases, or when administered in high enough concentrations orally, may hinder investigation into its potential or prevent its use under appropriate conditions. This problem could be resolved if LT could be "detoxified" without diminishing the adjuvant properties of the molecules. In order to appreciate how this might be accomplished, it is necessary to further analyze the mechanism of action of the LT and CT and the structural and functional relationships of these molecules. As indicated previously, both LT and CT are synthesized as multisubunit toxins with A and B components. After the initial interaction of the toxin with the host cell membrane receptor, the B region facilitates the penetration of the A-subunit through the cell membrane. On thiol reduction, this A component dissociates into two smaller polypeptide chains. One of these, the $A_1$ piece, catalyzes the ADP-ribosylation of the stimulatory GTP-binding protein ($G_s$) in the adenylate cyclase enzyme complex on the basolateral surface of the epithelial cell and this results in increasing intracellular levels of cAMP. The resulting increase in cAMP causes secretion of water and electrolytes into the small intestine through interaction with two cAMP-sensitive ion transport mechanisms involving 1) NaCl co-transport across the brush border of villous epithelial cells, and 2) electrogenic $Na^+$ dependent $Cl^-$secretion by crypt cells [Field, 1980, In: Secretory diarrhea, Field et al. (ed.), Waverly Press, Baltimore. p.21–30]. The A subunit is also the principal moiety associated with immune enhancement by these toxins. This subunit then becomes a likely target for manipulation in order to dissociate the toxic and immunologic functions of the molecules. A recent report by Lycke et al. [Lycke et al., 1992, Eur. J. Immunol. 22:2277–2281] makes it clear that alterations that affect the ADP-ribosylating enzymatic activity of the toxin and alter the ability to increase intracellular levels of cAMP also prevent the molecule from functioning as an adjuvant. Consequently, another approach to detoxification must be explored.

3. SUMMARY OF THE INVENTION

The present invention is based on the surprising observation that a mutant form of LT, which has reduced toxicity and is devoid of in vitro ADP-ribosyltransferase activity, still retains its activity as an immunological adjuvant when administered, preferably through a mucosal surface, e.g. orally, nasally, etc. The mutant form of LT differs from the wild-type by a single amino acid substitution, $Arg_{192}$-$Gly_{192}$, rendering a trypsin sensitive site insensitive. The loss of the proteolytic site prevents the proteolytic processing of the A subunit into its toxic form. Native LT is not toxic when first isolated from the bacterium but has the potential to be fully toxic when exposed to proteases such as those found in the mammalian intestine. The mutant form of LT no longer has the potential to become toxic due to proteolytic activation. This mutant LT (hereinafter mLT) retains the capability of enhancing an animal's immune response (e.g., IgG, IgA, cell mediated immunity) to an antigen unrelated to LT or mLT with no toxic side effects at an adjuvant effective dose. Experimental evidence shows that mLT has utility as an adjuvant for administered antigens; such administration results in the production of serum IgG and/or mucosal sIgA and cell mediated immune responses against the antigen with which the mLT is delivered.

The present invention provides a method for induction of a serum and/or mucosal immune response in a host to any antigen administered, by way of example and not by way of limitation, by an intradermal, intramuscular, intraperitoneal, intravenous, subcutaneous, transdermal, epidural, pulmonary, oral, nasal, gastric, intestinal, rectal, vaginal, or urethral route. Preferably, the route of administration is a mucosal route of administration, i.e., through a mucosal membrane or surface, such as an oral, nasal, gastric, intestinal, rectal, vaginal or urethral route. More preferably, the mucosal route of administration is through an oral or nasal membrane.

The methods of the present invention comprise administering to the host an effective amount of mLT in conjunction with administration of an effective amount of the antigen. Preferably, the antigen and the mLT are administered initially in a simultaneous dose.

The present method and compositions provide an improved mode of immunization for development of serum and mucosal antibodies and cell mediated immune responses against pathogenic microorganisms. Production of IgA antibody responses against pathogenic microorganisms which penetrate or invade across mucosal surfaces can be directed to that surface, while a significant serum antibody and cell mediated immune responses can be developed to prevent infection by pathogenic microorganisms against which serum antibody or cell mediated immunity is protective. The present invention is useful for any specific antigen where a specific neutralizing antibody or cell mediated immune response would be useful in ablating the physiological or disease state associated with that antigen.

The present invention also provides a composition useful as a component of a vaccine against enterotoxic bacterial organisms expressing cholera-like enterotoxins and methods for its use.

The invention also provides a composition useful in these methods. The composition comprises an effective amount of mLT in combination with an effective amount of antigen.

4. BRIEF DESCRIPTION OF THE FIGURES

The present invention may be understood more fully by reference to the following detailed description of the invention, examples of specific embodiments of the invention and the appended figures in which:

FIG. 1 is a schematic diagram of the plasmid pBD94, which encodes both subunits A and B under the control of the lac promoter. Plasmid pBD95 contains the single base substitution at amino acid residue 192 of subunit A, coding for Gly rather than Arg, which preserves the reading frame but eliminates the proteolytic site. The amino acid sequence corresponding to the region of trypsin sensitivity and the site of the amino acid substitution $Arg_{192}$-$Gly_{192}$ is shown.

FIG. 4 illustrates the ability of mLT to act as an immunological adjuvant.

FIG. 5 is an experimental demonstration that mLT retains the ability to prevent induction of oral tolerance to LT.

5. DETAILED DESCRIPTION OF THE INVENTION

Figure 1:
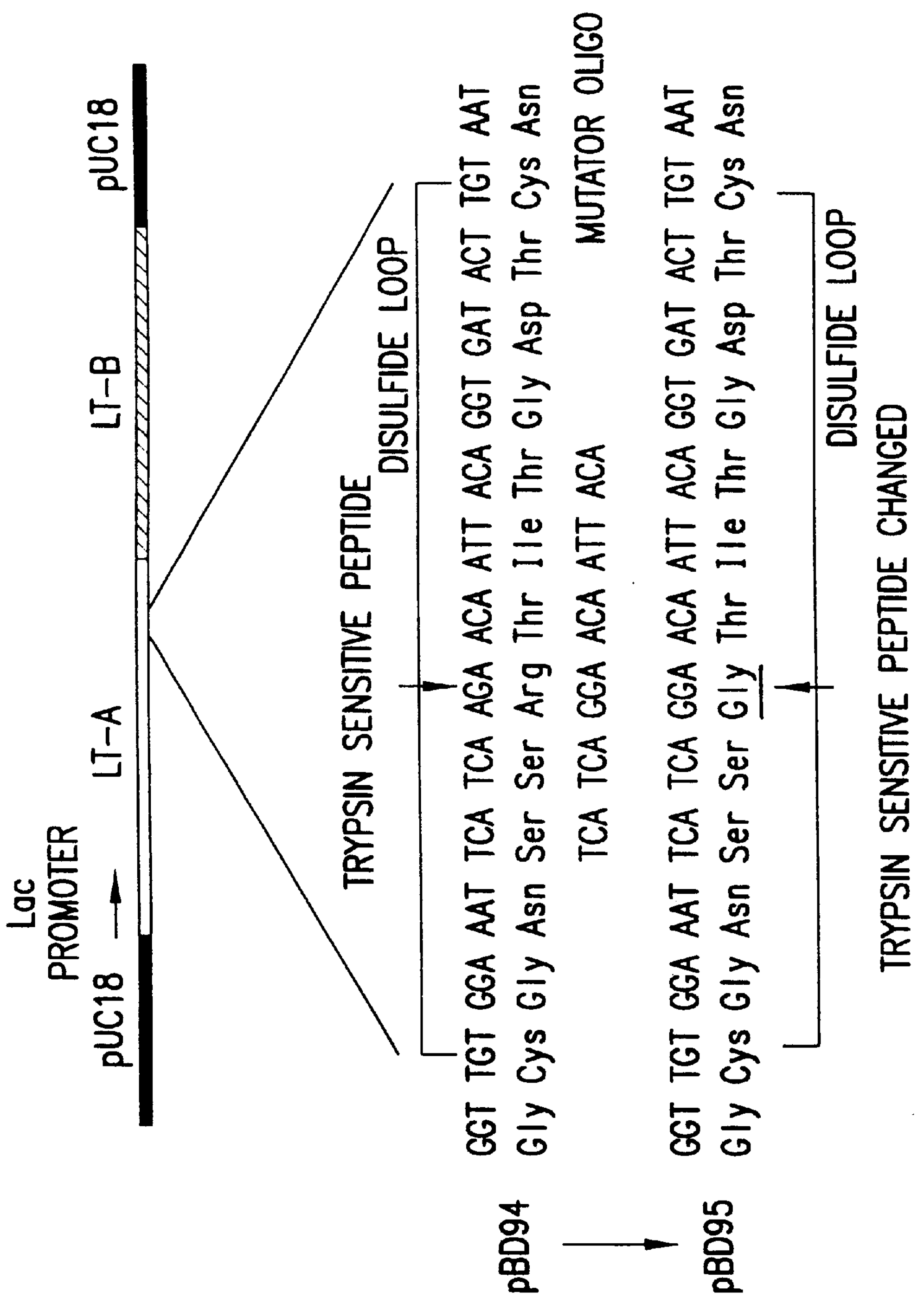

The present invention encompasses a composition and methods for its use to promote the production of mucosal and serum antibodies and cell mediated immune responses against antigens that are administered simultaneously with a genetically modified bacterial toxin. The mode of administration may be, by way of example and not by way of limitation, by an intradermal, intramuscular, intraperitoneal, intravenous, subcutaneous, transdermal, epidural, pulmonary, oral, nasal, gastric, intestinal, rectal, vaginal, or urethral route. Preferably, the route of administration is a mucosal route of administration, i.e., through a mucosal membrane or surface, such as an oral, nasal, gastric, intestinal, rectal, vaginal or urethral route. More preferably, the mucosal route of administration is through an oral or nasal membrane. The modified toxin is a form of the heat-labile enterotoxin (LT) of *E. coli* which through genetic engineering has lost its trypsin sensitive site, rendering the molecule non-toxic at adjuvant effective doses, but yet, unexpectedly, retains its ability to act as an immunological adjuvant. The mutant LT is herein termed "mLT". The invention is based on the discovery that mLT is as effective as LT as an immunological adjuvant, an unexpected and surprising result. mLT no longer has the enzymatic activity of ADP-ribosylation because the A subunit can no longer be proteolytically processed. In contrast to published studies of Lycke and colleagues, which made it clear that alterations that affect the ADP-ribosylating activity of LT also prevent the molecule from functioning as an immunologic adjuvant [Lycke et al., 1992, Eur. J. Immunol. 22:2277–2281], the presently described mLT retains activity as an immunological adjuvant although, as demonstrated in the examples, it does not have in vitro ADP-ribosylating activity and has no enterotoxicity at an adjuvant effective dose.

The novel mutant form of the heat-labile enterotoxin of *E. coli,* mLT, described herein, behaves as an adjuvant and elicits the production of both serum IgG and mucosal sIgA and cell mediated immune responses against antigens with which it is delivered. The utility of this surprising discovery is that an adjuvant effective amount of mLT may be utilized in an effective immunization program against a variety of pathogens involving the administration of an effective amount of mLT adjuvant in admixture with killed or attenuated pathogens or relevant virulence determinants of specific pathogens with no fear of the real or potential toxic side-effects associated with oral administration of CT or LT.

The present invention supersedes the prior art in that the present invention may be used in a variety of immunological applications in which CT, LT, or subunits of CT or LT may have been used. With the use of mLT, however, there are no real or potential side-effects, such as diarrhea, associated with its use. In contrast to LT, which although not toxic when first isolated from the bacterium, has the potential to be fully toxic when exposed to proteases such as those found in the mammalian intestine, mLT does not have the potential to become toxic due to proteolytic activation.

Another embodiment of the present invention is as a component of a vaccine against enterotoxic organisms which express cholera-like toxins. The present inventors have shown that mLT is not subject to orally induced immune tolerance when administered (see below), therefore mLT can function and is highly desired as a component of vaccines directed against enterotoxic organisms. Current technology provides for vaccines against cholera-like toxin expressing organisms containing killed whole cells and the B subunit of the toxin. By replacing the B subunit with mLT in the vaccine, the vaccine is improved in two different ways. First, mLT, which has both the A and B subunits will now induce an immune response not only to the B subunit but to the A subunit as well. This provides for more epitopes for effective neutralization. Second, the adjuvant activity inherent in mLT will enhance the immune response against the killed whole cell component of the vaccine.

Further, other investigators [Häse et al., 1994, Infect. Immun. 62:3051–3057] have shown that the A subunit, modified so that it is no longer toxic by altering the active site of the ADP-ribosylating enzymatic activity, (as opposed to the proteolytic site which is the subject of the current invention) can induce an immune response against the wild type A subunit. However, the A subunit so modified now lacks immunologic adjuvant activity and is therefore less desirable as a vaccine component than mLT.

Moreover, since antibodies against mLT cross-react with LT and CT, mLT can be used in vaccines directed against many types of enterotoxic bacterial organisms that express cholera-like toxins, such as Escherichia spp. and Vibrio spp.

5.1. Production of mLT

The wild-type LT toxin is encoded on a naturally occurring plasmid found in strains of enterotoxigenic *E. coli* capable of producing this toxin. The present inventors had previously cloned the LT gene from a human isolate of *E. coli* designated H10407. This subclone consists of a 5.2 kb DNA fragment from the enterotoxin plasmid of H10407 inserted into the PstI site of plasmid pBR322 [Clements et al., 1983, Infect. Immun. 40:653]. This recombinant plasmid, designated pDF82, has been extensively characterized and expresses LT under control of the native LT promoter. The next step in this process was to place the LT gene under the control of a strong promoter, in this case the lac promoter on plasmid pUC18. This was accomplished by isolating the genes for LT-A and LT-B separately and recombining them in a cassette in the vector plasmid. This was an important step because it permitted purification of reasonable quantities of LT and derived mutants for subsequent analysis. This plasmid, designated pBD94, is shown diagrammatically in FIG. 1.

Both CT and LT are synthesized with a trypsin sensitive peptide bond that joins the $A_1$ and $A_2$ pieces. This peptide bond must be nicked for the molecule to be “toxic”. This is also true for diphtheria toxin, the prototypic A-B toxin, and for a variety of other bacterial toxins. If the $A_1$—$A_2$ bond of CT or LT is not removed, either by bacterial proteases or intestinal proteases in the lumen of the bowel, the $A_1$ piece cannot reach its target on the basolateral surface of the intestinal epithelial cell. In contrast to CT, LT is not fully biologically active when first isolated from the cell. LT also requires proteolysis to be fully active and the proteolytic activation does not occur inside of the bacterium. Therefore, one means of altering the toxicity of the molecule without affecting the NAD-binding site associated with ADP-ribosylating enzymatic activity would be to remove by genetic manipulation the trypsin sensitive amino acids that join the $A_1$ and $A_2$ components of the A subunit. If the molecule cannot be proteolytically cleaved, it will not be toxic. One skilled in the art would predict that the molecule should, however, retain its ADP-ribosylating enzymatic activity and consequently, its adjuvant function.

FIG. 1 shows the sequence of the disulfide subtended region that separates the $A_1$ and $A_2$ pieces. Within this region is a single Arginine residue which is believed to be the site of cleavage necessary to activate the toxic properties of the molecule. This region was changed by site-directed mutagenesis in such a way as to render the molecule insensitive to proteolytic digestion and, consequently, nontoxic.

Site-directed mutagenesis is accomplished by hybridizing to single stranded DNA a synthetic oligonucleotide which is complementary to the single stranded template except for a region of mismatch near the center. It is this region that contains the desired nucleotide change or changes. Following hybridization with the single stranded target DNA, the oligonucleotide is extended with DNA polymerase to create a double stranded structure. The nick is then sealed with DNA ligase and the duplex structure is transformed into an *E. coli* host. The theoretical yield of mutants using this procedure is 50% due to the semi-conservative mode of DNA replication. In practice, the yield is much lower. There are, however, a number of methods available to improve yield and to select for oligonucleotide directed mutants. The system employed utilized a second mutagenic oligonucleotide to create altered restriction sites in a double mutation strategy.

The next step was to substitute another amino acid for Arg (i.e., GGA=Gly replaces AGA=Arg), thus preserving the reading frame while eliminating the proteolytic site. mLT was then purified by agarose affinity chromatography from one mutant (pBD95) which had been confirmed by sequencing. Alternate methods of purification will be apparent to those skilled in the art. This mutant LT, designated $LT_{(R192G)}$ was then examined by SDS-polyacrylamide gel electrophoresis for modification of the trypsin sensitive bond. Samples were examined with and without exposure to trypsin and compared with native (unmodified) LT. mLT does not dissociate into $A_1$ and $A_2$ when incubated with trypsin, thereby indicating that sensitivity to this protease this has been removed.

5.2. Mode of Administration of mLT and Unrelated Antigens

In accordance with the present invention, mLT can be administered in conjunction with any biologically relevant antigen and/or vaccine, such that an increased immune response to said antigen and/or vaccine is achieved. In a preferred embodiment, the mLT and antigen are administered simultaneously in a pharmaceutical composition comprising an effective amount of mLT and an effective amount of antigen. The mode of administration may be, by way of example and not by way of limitation, by an intradermal, intramuscular, intraperitoneal, intravenous, subcutaneous, transdermal, epidural, pulmonary, oral, nasal, gastric, intestinal, rectal, vaginal, or urethral route. Preferably, the route of administration is a mucosal route of administration, i.e., through a mucosal membrane or surface, such as an oral, nasal, gastric, intestinal, rectal, vaginal or urethral route. More preferably, the mucosal route of administration is through an oral or nasal membrane.

The respective amounts of mLT and antigen will vary depending upon the identity of the antigen employed and the species of animal to be immunized. In one embodiment, the initial administration of mLT and antigen is followed by a boost of the relevant antigen. In another embodiment no boost is given. The timing of boosting may vary, depending on the antigen and the species being treated. The modifications in dosage range and timing of boosting for any given species and antigen are readily determinable by routine experimentation. The boost may be of antigen alone or in combination with mLT. The mode of administration of the boost may either be oral, nasal, or parenteral.

The methods and compositions of the present invention are intended for use both in immature and mature vertebrates, in particular birds, mammals, and humans. Useful antigens, as examples and not by way of limitation, would include antigens from pathogenic strains of bacteria (*Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis,* Mycoplasma spp., *Rickettsia prowazeki, Rickettsia tsutsugumushi,* Chlamydia spp., *Helicobacter pylori;* pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms) either presented to the immune system in whole cell form or in part isolated from media cultures designed to grow said organisms which are well known in the art or relevant antigens from said organisms obtained by genetic engineering techniques or by chemical synthesis.

Other relevant antigens would be pathogenic viruses (as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus) either presented to the immune system in whole or in part isolated from media cultures designed to grow such viruses which are well known in the art or relevant antigens therefrom obtained by genetic engineering techniques or by chemical synthesis.

Further examples of relevant antigens include, but are not limited to, vaccines. Examples of such vaccines include, but are not limited to, influenza vaccine, pertussis vaccine, diphtheria and tetanus toxoid combined with pertussis vaccine, hepatitis A vaccine, hepatitis B vaccine, hepatitis C vaccine, hepatitis E vaccine, Japanese encephalitis vaccine, herpes vaccine, measles vaccine, rubella vaccine, mumps vaccine, mixed vaccine of measles, mumps and rubella, papillomavirus vaccine, parvovirus vaccine, respiratory syncytial virus vaccine, Lyme disease vaccine, polio vaccine, malaria vaccine, varicella vaccine, gonorrhea vaccine, HIV vaccine, schistosomiasis vaccine, rotavirus vaccine, mycoplasma vaccine, pneumococcal vaccine, meningococcal vaccine and others. These can be produced by known common processes. In general, such vaccines comprise either the entire organism or virus grown and isolated by techniques well known to the skilled artisan or comprise relevant antigens of these organisms or viruses which are produced by genetic engineering techniques or chemical synthesis. Their production is illustrated by, but not limited to, as follows:

Influenza vaccine: a vaccine comprising the whole or part of hemagglutinin, neuraminidase, nucleoprotein and matrix protein which are obtainable by purifying a virus, which is grown in embryonated eggs, with ether and detergent, or by genetic engineering techniques or chemical synthesis.

Pertussis vaccine: a vaccine comprising the whole or a part of pertussis toxin, hemagglutinin and K-agglutinin which are obtained from avirulent toxin (with formalin) which is extracted by salting-out or ultracentrifugation from the culture broth or bacterial cells of *Bordetella pertussis,* or by genetic engineering techniques or chemical synthesis.

Diphtheria and tetanus toxoid combined with pertussis vaccine: a vaccine mixed with pertussis vaccine, diphtheria and tetanus toxoid.

Japanese encephalitis vaccine: a vaccine comprising the whole or part of an antigenic protein which is obtained by culturing a virus intracerebrally in mice and purifying the virus particles by centrifugation or ethyl alcohol and inactivating the same, or by genetic engineering techniques or chemical synthesis.

Hepatitis B vaccine: a vaccine comprising the whole or part of an antigen protein which is obtained by isolating and purifying the HBs antigen by salting-out or ultracentrifugation, obtained from hepatitis carrying blood, or by genetic engineering techniques or by chemical synthesis.

Measles vaccine: a vaccine comprising the whole or part of a virus grown in a cultured chick embryo cells or embryonated egg, or a protective antigen obtained by genetic engineering or chemical synthesis.

Rubella vaccine: a vaccine comprising the whole or part of a virus grown in cultured chick embryo cells or embryonated egg, or a protective antigen obtained by genetic engineering techniques or chemical synthesis.

Mumps vaccine: a vaccine comprising the whole or part of a virus grown in cultured rabbit cells or embryonated egg, or a protective antigen obtained by genetic engineering techniques or chemical synthesis.

Mixed vaccine of measles, rubella and mumps: a vaccine produced by mixing measles, rubella and mumps vaccines.

Rota vaccine: a vaccine comprising the whole or part of a virus grown in cultured MA 104 cells or isolated from the patient's feces, or a protective antigen obtained by genetic engineering techniques or chemical synthesis.

Mycoplasma vaccine: a vaccine comprising the whole or part of mycoplasma cells grown in a liquid culture medium for mycoplasma or a protective antigen obtained by genetic engineering techniques or chemical synthesis.

Those conditions for which effective prevention may be achieved by the present method will be obvious to the skilled artisan.

The vaccine preparation compositions of the present invention can be prepared by mixing the above illustrated antigens and/or vaccines with mLT at a desired ratio. The preparation should be conducted strictly aseptically, and each component should also be aseptic. Pyrogens or allergens should naturally be removed as completely as possible. The antigen preparation of the present invention can be used by preparing the antigen per se and the mLT separately.

Further, the present invention encompasses a kit comprising an effective amount of antigen and an adjuvant effective amount of mLT. In use, the components of the kit can either first be mixed together and then administered orally or the components can be administered orally separately within a short time of each other.

The vaccine preparation compositions of the present invention can be combined with either a liquid or solid pharmaceutical carrier, and the compositions can be in the form of tablets, capsules, powders, granules, suspensions or solutions. The compositions can also contain suitable preservatives, coloring and flavoring agents, or agents that produce slow release such as encapsulating agents such as liposomes, microparticles, microcapsules, etc. Potential carriers that can be used in the preparation of the pharmaceutical compositions of this invention include, but are not limited to, gelatin, gelatin capsules, sugars, cellulose derivations such as sodium carboxymethyl cellulose, talc, magnesium stearate, vegetable oil such as peanut oil, etc., glycerin, glycerol, sorbitol, agar, water, saline, buffered saline, sterile isotonic aqueous buffer, and combinations thereof. Carriers may also serve as a binder to facilitate tabletting of the compositions for convenient oral administration. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The mode of administration of the vaccine preparation compositions of the invention include, but are not limited to an intradermal, intramuscular, intraperitoneal, intravenous, subcutaneous, transdermal, epidural, pulmonary, oral, nasal, gastric, intestinal, rectal, vaginal, or urethral route. Preferably, the route of administration is a mucosal route of administration, i.e., through a mucosal membrane or surface, such as an oral, nasal, gastric, intestinal, rectal, vaginal or urethral route. More preferably, the mucosal route of administration is through an oral qr nasal membrane.

The compounds may be administered in any convenient manner, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, by way of example and not by way of limitation, by topical application, by injection, by means of a catheter, by means of a suppository, or by means of an implant, the implant being of a porous, non-porous, or gelatinous material, including membranes, such as sialastic membranes, or fibers.

In another embodiment, the pharmaceutical compositions of the invention can be delivered in a vesicle, in particular a liposome [see Langer, 1990, Science 249:1527–1533; Treat et al., 1989, in *Liposomes in the Therapy of Infectious Disease and Cancer,* Lopez-Berestein and Fidler (eds.), Liss, New York, pp. 353–365; Lopez-Berestein, ibid., pp. 317–327; see generally ibid.].

In yet another embodiment, the pharmaceutical compositions of the invention can be delivered in a controlled release system. In one embodiment, a pump may be used [see Langer, supra; Sefton, 1987, *CRC Crit. Ref. Biomed. Eng.* 14: 201; Buchwald et al., 1980, Surgery 88: 507; Saudek et al., 1989, N. Engl. J. Med. 321: 574]. In another embodiment, polymeric materials can be used [see 1974, *Medical Applications of Controlled Release,* Langer and Wise (eds.), CRC Pres., Boca Raton, Fla.; 1984, *Controlled Drug Bioavailability, Drug Product Design and Performance,* Smolen and Ball (eds.), Wiley, New York; Ranger and Peppas, 1983, J. Macromol. Sci. Rev. Macromol. Chem. 23:61; see also Levy et al., 1985, Science 228: 190; During et al., 1989, *Ann. Neurol.* 25: 351; Howard et al., 1989, J. Neurosurg. 71: 105].

In yet another embodiment, a controlled release system can be placed in proximity of a mucosal target, thus requiring only a fraction of the systemic dose [see, e.g., Goodson, 1984, in *Medical Applications of Controlled Release,* supra, vol. 2, pp. 115–138].

Other controlled release systems are discussed in the review by Langer [1990, Science 249: 1527–1533].

The vaccine preparation compositions of this invention may be maintained in a stable storage form for ready use by lyophilization or by other means well known to those skilled in the art.

In one embodiment of the invention, a vaccine preparation composition of the invention is administered orally. For oral administration, the vaccine preparation may be reconstituted as a suspension in buffered saline, milk, or any other physiologically compatible liquid medium. The medium may be made more palatable by the addition of suitable coloring and flavoring agents as desired.

Oral administration of the vaccine preparation compositions may be preceded by an oral dosage of an effective amount of a gastric acid neutralizing agent. While many compounds could be used for this purpose, sodium bicarbonate is preferred. Alternatively, the vaccine compositions may be delivered in enteric coated capsules (i.e., capsules that dissolve only after passing through the stomach).

The ingredients can be supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

In a specific embodiment, a lyophilized mixture of an effective amount of antigen and an adjuvant effective amount of mLT of the invention is provided in a first container; a second container comprises diluent consisting of an aqueous solution of 50% glycerin, 0.25% phenol, and an antiseptic (e.g., 0.005% brilliant green).

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified antigens should be adjusted to an appropriate concentration, formulated with an adjuvant-effective amount of mLT and packaged for use. The immunogen may also be incorporated into liposomes, or conjugated to polysaccharides and/or other polymers for use in a vaccine formulation.

The following examples are presented for purposes of illustration only and are not intended to limit the scope of the invention in any way.

6. EXAMPLE 1

Characterization of mLT Activities

6.1. Construction of mLT

The wild-type LT toxin is encoded on a naturally occurring plasmid found in strains of enterotoxigenic *E. coli* capable of producing this toxin. The present inventors had previously cloned the LT gene from a human isolate of *E. coli* designated H10407. This subclone consists of a 5.2 kb DNA fragment from the enterotoxin plasmid of H10407 inserted into the PstI site of plasmid pBR322 [Clements et al., 1983, Infect. Immun. 40:653]. This recombinant plasmid, designated pDF82, has been extensively characterized and expresses LT under control of the native LT promoter. The next step in this process was to place the LT gene under the control of a strong promoter, in this case the lac promoter on plasmid pUC18. This was accomplished by isolating the genes for LT-A and LT-B separately and recombining them in a cassette in the vector plasmid. This was an important step because it permitted purification of reasonable quantities of LT and derived mutants for subsequent analysis. This plasmid, designated pBD94, is shown diagrammatically in FIG. 1.

Both CT and LT are synthesized with a trypsin sensitive peptide bond that joins the $A_1$ and $A_2$ pieces. This peptide bond must be nicked for the molecule to be "toxic". This is also true for diphtheria toxin, the prototypic A-B toxin, and for a variety of other bacterial toxins. If the $A_1$—$A_2$ bond is not removed, either by bacterial proteases or intestinal proteases in the lumen of the bowel, i.e., proteolytic processing or activation, the $A_1$ piece cannot reach its target on the basolateral surface of the intestinal epithelial cell. In contrast to CT, LT is not fully biologically active when first isolated from the cell. LT also requires proteolysis to be fully active and the proteolytic activation does not occur inside of the bacterium. Therefore, one means of altering the toxicity of the molecule without affecting the ADP-ribosylating enzymatic activity would be to remove by genetic manipulation the trypsin sensitive amino acids that join the $A_1$ and $A_2$ components of the A subunit. If the molecule cannot be proteolytically cleaved, it will not be toxic. One skilled in the art would predict that the molecule should, however, retain its ADP-ribosylating enzymatic activity and consequently, its adjuvant function.

FIG. 1 shows the sequence of the disulfide subtended region that separates the $A_1$ and $A_2$ pieces. Within this region is a single Arginine residue which is believed to be the site of cleavage necessary to activate the toxic properties of the molecule. This region was changed by site-directed mutagenesis in such a way as to render the molecule insensitive to proteolytic digestion and, consequently, non-toxic.

Site-directed mutagenesis is accomplished by hybridizing to single stranded DNA a synthetic oligonucleotide which is complementary to the single stranded template except for a region of mismatch near the center. It is this region that contains the desired nucleotide change or changes. Following hybridization with the single stranded target DNA, the oligonucleotide is extended with DNA polymerase to create a double stranded structure. The nick is then sealed with DNA ligase and the duplex structure is transformed into an *E. coli* host. The theoretical yield of mutants using this procedure is 50% due to the semi-conservative mode of DNA replication. In practice, the yield is much lower. There are, however, a number of methods available to improve yield and to select for oligonucleotide directed mutants. The system employed utilized a second mutagenic oligonucleotide to create altered restriction sites in a double mutation strategy.

The next step was to substitute another amino acid for Arg (i.e., GGA=Gly replaces AGA=Arg), thus preserving the reading frame while eliminating the proteolytic site. mLT was then purified by agarose affinity chromatography from one mutant (pBD95) which had been confirmed by sequencing. Alternate methods of purification will be apparent to those skilled in the art. This mutant LT, designated $LT_{(R192G)}$ was then examined by SDS-polyacrylamide gel electrophoresis for modification of the trypsin sensitive bond. Samples were examined with and without exposure to trypsin and compared with native (unmodified) LT. mLT does not dissociate into $A_1$ and $A_2$ when incubated with trypsin, thereby indicating that sensitivity to protease h as been removed.

6.2. Effect of mLT on Y-1 Adrenal Cells

It would be predicted by one skilled in the art that mLT would not be active in the Y-1 adrenal cell assay. This prediction would be based upon previous findings [Clements and Finkelstein, 1979, Infect. Immun. 24:760–769] that un-nicked LT was more than 1,000 fold less active in this assay system than was CT and that trypsin treatment activated LT to the same level of biological activity as CT in this assay. It was presumed that the residual activity of LT observed in this assay in the absence of trypsin activation was a function of some residual protease activity which could not be accounted for. For instance, trypsin is used in the process of subculturing Y-1 adrenal cells. It was therefore assumed that LT that could not be nicked would be completely inactive in the Y-1 adrenal cell assay. Results are shown in Table I.

TABLE I

| Toxin | Trypsin Activated | Specific Activity[a] |
|---|---|---|
| Cholera Toxin | – | 15 |
| LT | – | 60 |
| LT | + | 15 |
| $LT_{(R192G)}$ | – | 48,800 |
| $LT_{(R192G)}$ | + | 48,800 |

[a]Minimum dose (picograms per well) required to produce (>50%) cell rounding.

Table I demonstrates the unexpected finding that mLT retained a basal level of activity in the Y-1 adrenal cell assay even though it could not be proteolytically processed. As shown in Table I, CT and native LT treated with trypsin have the same level of activity (15 pg) on Y-1 adrenal cells. By contrast, mLT (48,000 pg) was >1,000-fold less active than CT or native LT and could not be activated by trypsin. The residual basal activity undoubtedly reflects a different and heretofore unknown pathway of adrenal cell activation than that requiring separation of the $A_1$—$A_2$ linkage.

6.3. ADP-Ribosylating Enzymatic Activity of mLT

Figure 2:
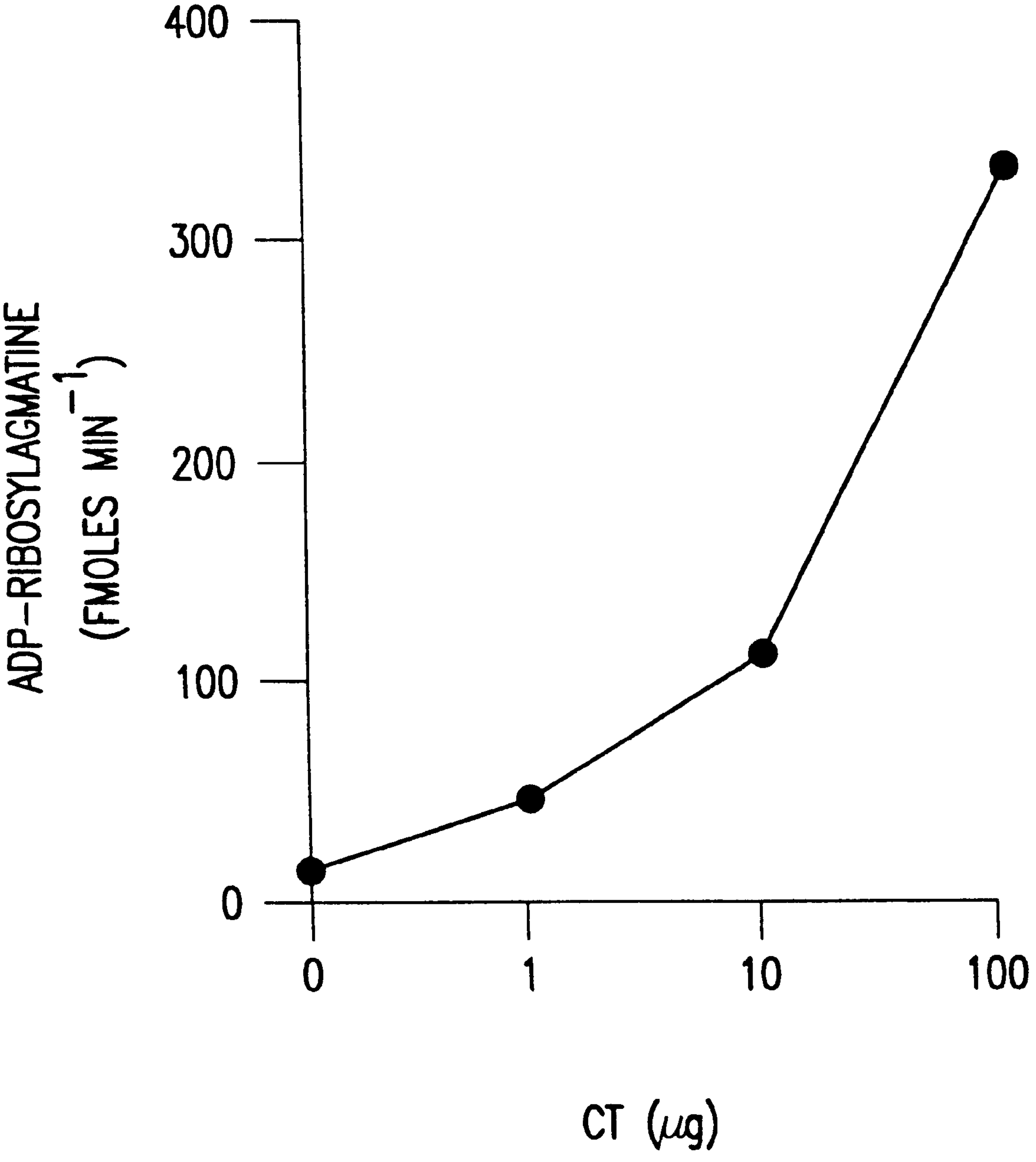
FIG. 2 is a graphic demonstration of the dose-dependent increase in the levels of ADP-ribosylagmatine as a function of increasing amounts of CT.

Because the mutation replacing $Arg_{192}$ with $Gly_{192}$ does not alter the enzymatic site of the $A_1$ moiety, one skilled in the art would predict that mLT would retain its ADP-ribosylating enzymatic activity. To examine this property, the NAD-Agmatine ADP-ribosyltransferase Assay was employed [Moss et al., 1993, J. Biol. Chem. 268:6383–6387]. As shown in FIG. 2, CT produces a dose-dependent increase in the levels of ADP-ribosylagmatine, a function of the ADP-ribosyltransferase activity of this molecule.

TABLE II

ADP-Ribosyltransferase Activity of CT, native LT, and $LT_{(R192G)}$

| Experiment | 1 | 2 | 3 | 4 | Mean ± SEM |
|---|---|---|---|---|---|
| No Toxin | ND | 9.12 | 5.63 | 14.17 | 9.64 ± 2.48 |
| 1 μgCT | ND | 17.81 | 17.60 | 25.75 | 20.39 ± 2.68 |
| 10 μgCT | ND | 107.32 | 111.28 | 104.04 | 107.55 ± 2.09 |
| 100 μgCT | 351.55 | 361.73 | 308.09 | ND | 340.46 ± 16.45 |
| 100 μgLT | 17.32 | 14.48 | 13.86 | ND | 15.22 ± 1.07 |
| 100 μgLT + Trypsin | 164.10 | 189.89 | 152.96 | ND | 168.98 ± 10.94 |
| 100 μg $LT_{(R192G)}$ | 14.58 | 12.34 | 9.30 | ND | 12.07 ± 1.53 |
| 100 μg $LT_{(R192G)}$ + Trypsin | 14.73 | 8.90 | 10.47 | ND | 11.37 ± 1.74 |

ND = Not Done
data expressed in fMoles $min^{-1}$

Table II demonstrates in tabular form the unexpected finding that mLT lacked any detectable ADP-ribosylating enzymatic activity, with or without trypsin activation, even though the enzymatic site had not been altered and there was a demonstratable basal level of activity in the Y-1 adrenal cell assay.

6.4. Enterotoxic Activity of mLT

Figure 3:
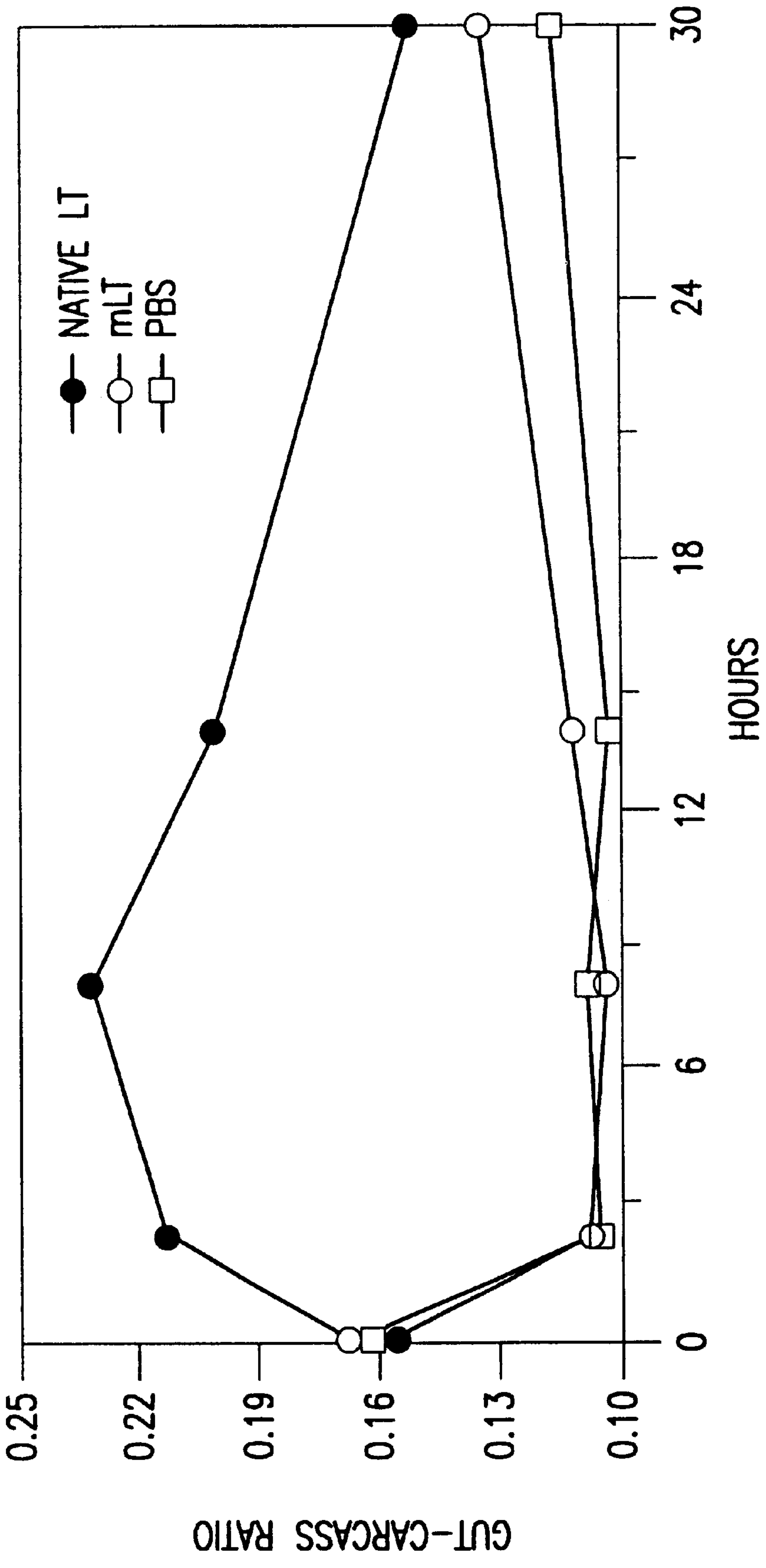
FIG. 3 shows the fluid accumulation after feeding 125 $\mu$g of native LT but not after feeding 125 $\mu$g of mLT to mice. The gut-carcass ratio is defined as the intestinal weight divided by the remaining carcass weight.

Because of the unexpected finding that mLT lacks any detectable ADP-ribosylating enzymatic activity, with or without trypsin activation, even though the enzymatic site has not been altered and the additional finding that there is a basal level of activity in the Y-1 adrenal cell assay, it was unclear whether mLT would retain any of its enterotoxic properties. An ideal adjuvant formulation of mLT would retain its ability to act as an immunological adjuvant but would lack the real or potential side-effects, such as diarrhea, associated with the use of LT or CT. FIG. 3 demonstrates that mLT does not induce net fluid secretion in the patent mouse model, even at a dose of 125 μg. This dose is more than five times the adjuvant effective dose for LT in this model. Importantly, the potential toxicity of native LT can be seen at this level.

6.5. Adjuvant Activity of mLT

One skilled in the art would predict that since mLT possessed no demonstrable ADP-ribosyltransferase activity and is not enterotoxic, it would lack adjuvant activity. This prediction would be based upon the report by Lycke et al. [Lycke et al., 1992, Eur. J. Immunol. 22:2277–2281] where it is made clear that alterations that affect the ADP-ribosylating enzymatic activity of the toxin and alter the ability to increase intracellular levels of cAMP also prevent the molecule from functioning as an adjuvant. As demonstrated above, mLT has no ADP-ribosylating enzymatic activity and only some undefined basal activity in Y-1 adrenal cells, and induces no net fluid secretion in the patent mouse model.

In order to examine the adjuvant activity of mLT the following experiment was performed. Three groups of BALB/c mice were immunized. Animals were inoculated intragastrically with a blunt tipped feeding needle (Popper & Sons, Inc., New Hyde Park, N.Y.). On day 0, each group was immunized orally as follows: Group A received 0.5 ml of PBS containing mg of OVA, Group B received 0.5 ml of PBS containing 5 mg of OVA and 25 μg of native LT, and Group C received 0.5 ml of PBS containing 5 mg of OVA and 25 μg of mLT. Each regimen was administered again on days 7 and 14. On day 21, all animals ere boosted i.p. with 1 μg of OVA in 20% Maalox. One week after the i.p. inoculation animals were sacrificed and assayed for serum IgG and mucosal IgA antibodies directed against OVA and LT by ELISA.

Reagents and antisera for the ELISA were obtained from Sigma Chemical Co. Samples for ELISA were serially diluted in phosphate buffered saline (pH 7.2)–0.05% TWEEN™ (Polyoxyethelenesorbitan monolaurate) (PBS-TWEEN™). For anti-LT determinations, microtiter plates were precoated with 1.5 μg per well of mixed gangliosides (Type III), then with 1 μg per well of purified LT. Anti-OVA responses were determined on microtiter plates precoated with 10 μg per well of OVA. Serum anti-LT and anti-OVA were determined with rabbit antiserum against mouse IgG conjugated to alkaline phosphatase. Mucosal anti-LT and anti-OVA IgA were assayed with goat antiserum against mouse IgA [alpha-chain specific] followed by rabbit antiserum against goat IgG conjugated to alkaline phosphatase. Reactions were stopped with 3N NaOH. Values for IgG and IgA were determined from a standard curve with purified mouse myeloma proteins (MOPC 315, γA (IgAλ2); MOPC 21, γG1: Litton Bionetics, Inc., Charleston, S.C.).

6.5.1. Serum IgG Anti-OVA

Figure 4A:
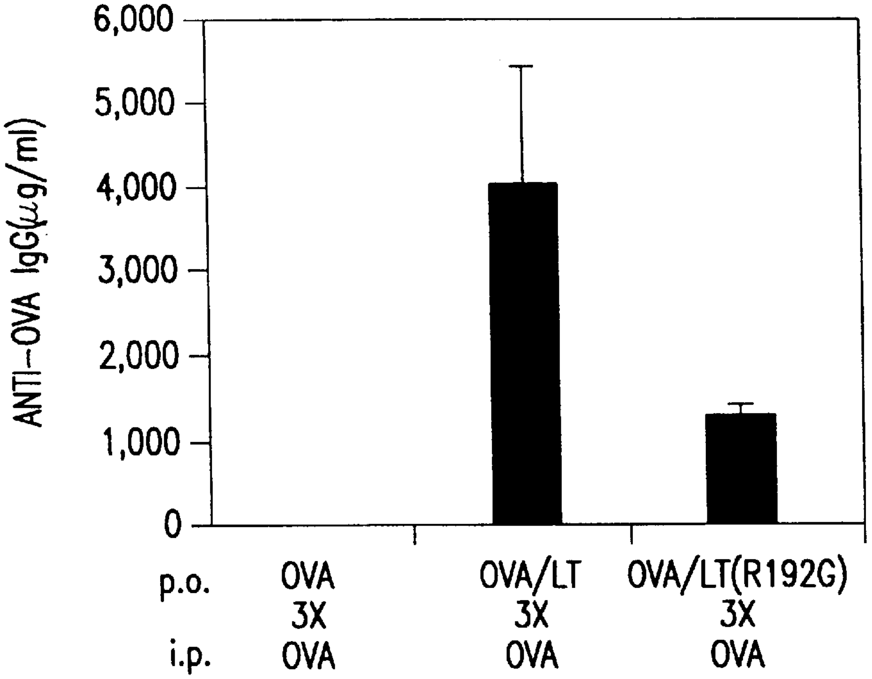
FIG. 4A shows the ability of mLT to induce a serum IgG response to OVA.

As shown in the FIG. 4A, animals immunized orally with OVA and LT developed a significantly higher serum IgG anti-OVA response following subsequent parenteral immunization with OVA (4,058 μg/ml) than those immunized orally with OVA alone and subsequently immunized parenterally with OVA (No detectable anti-OVA response) (Student t-test p=0.031). Significantly, animals immunized orally with OVA and mLT also developed a significantly higher serum IgG anti-OVA response following subsequent parenteral immunization with OVA (1,338 μg/ml) than those immunized orally with OVA alone and subsequently immunized parenterally with OVA (No detectable anti-OVA response) (Student t-test p=0.0007).

6.5.2. Mucosal sIgA Anti-OVA

Figure 4B:
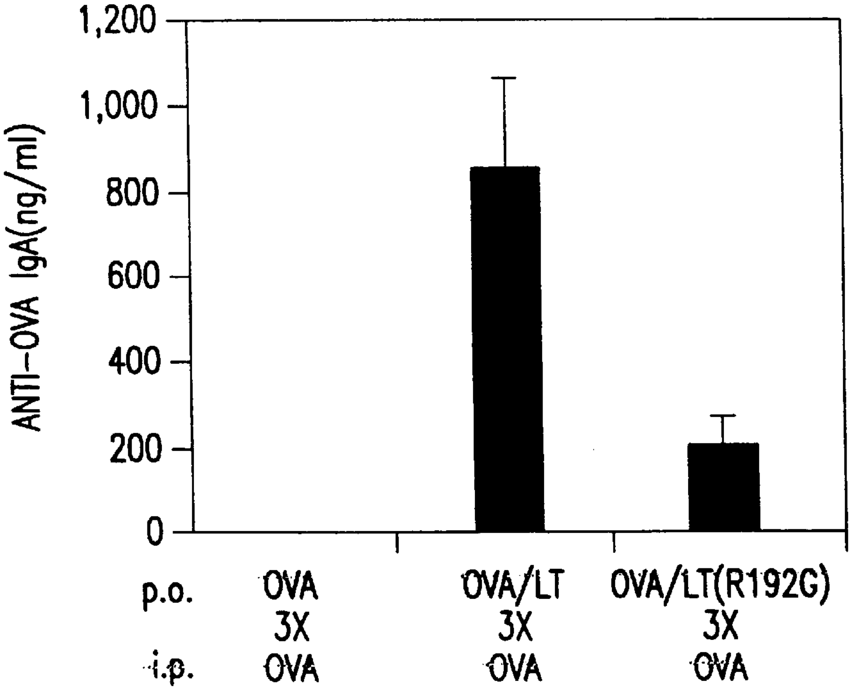
FIG. 4B shows the ability of mLT to induce a mucosal sIgA response to OVA.

As shown in the FIG. 4B, similar results were obtained when anti-OVA IgA responses were compared within these same groups of animals. Animals immunized orally with OVA and LT developed a significantly higher mucosal IgA anti-OVA response following subsequent parenteral immunization with OVA (869 ng/ml) than those immunized orally with OVA alone and subsequently immunized parenterally with OVA (No detectable anti-OVA response) (Student t-test p=0.0131). As above, animals immunized orally with OVA and mLT also developed a significantly higher mucosal IgA anti-OVA response following subsequent parenteral immunization with OVA (230 ng/ml) than those immunized orally with OVA alone and subsequently immunized parenterally with OVA (No detectable anti-OVA response) (Student t-test p=0.0189).

6.5.3. Serum IgG Anti-LT

Figure 5A:
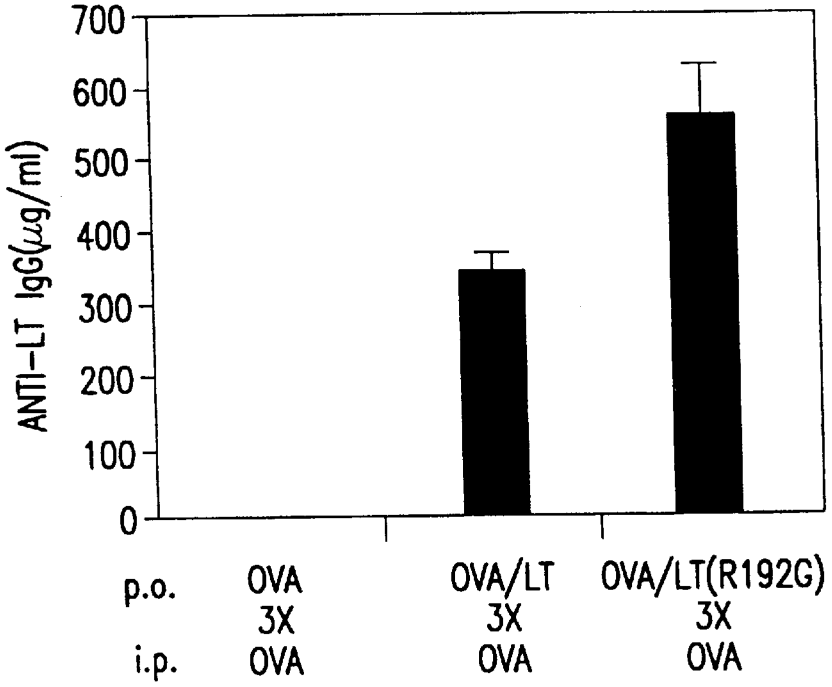
FIG. 5A shows the ability of mLT to induce a serum IgG response to LT.

The ability of LT and mLT to elicit an anti-LT antibody response in these same animals was also examined. This was important in that it would provide an indication of whether the mutant LT was able to prevent induction of tolerance to itself in addition to functioning as an adjuvant for other proteins. As shown in FIG. 5A, animals immunized orally with OVA and LT developed a significantly higher serum IgG anti-LT response following subsequent parenteral immunization with OVA (342 μg/ml) than those immunized orally with OVA alone and subsequently immunized parenterally with OVA (No detectable anti-LT response) (Student t-test p=0.0005). Animals immunized orally with OVA and mLT also developed a significantly higher serum IgG anti-LT response following subsequent parenteral immunization with OVA (552 μg/ml) than those immunized orally with OVA alone and subsequently immunized parenterally with OVA (No detectable anti-LT response) (Student t-test p=0.0026).

6.5.4. Mucosal sIgA Anti-LT

Figure 5B:
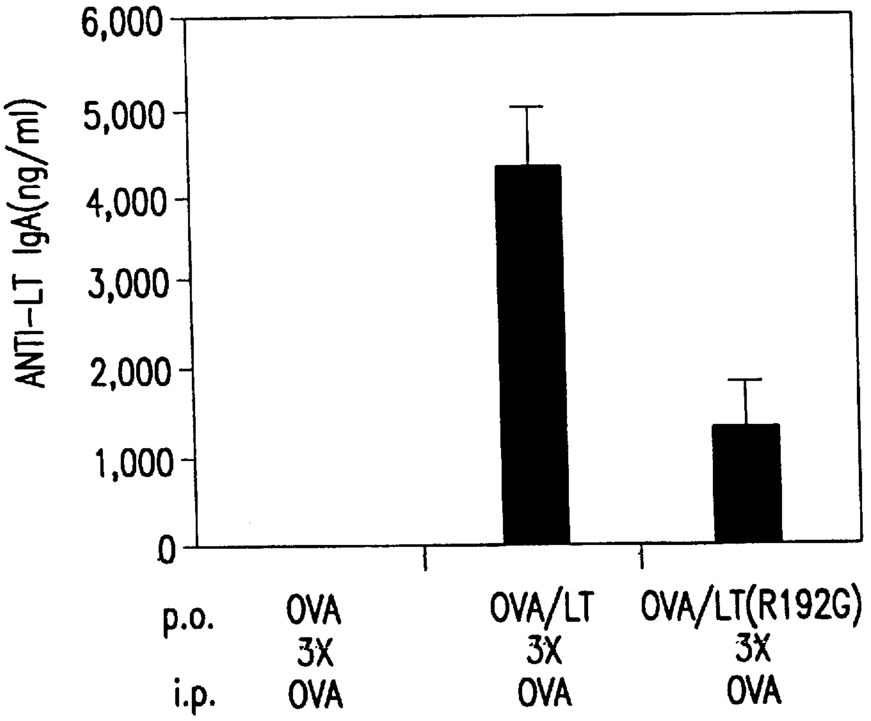
FIG. 5B shows the ability of mLT to induce a mucosal sIgA response to LT.

As shown in the FIG. 5B, similar results were obtained when anti-LT IgA responses were compared within these same groups of animals. Animals immunized orally with OVA and LT developed a significantly higher mucosal IgA anti-LT response following subsequent parenteral immunization with OVA (4,328 ng/ml) than those immunized orally with OVA alone and subsequently immunized parenterally with OVA (No detectable anti-LT response) (Student t-test p=0.0047). As above, animals immunized orally with OVA and mLT also developed a significantly higher mucosal IgA anti-LT response following subsequent parenteral immunization with OVA (1,463 ng/ml) than those immunized orally with OVA alone and subsequently immunized parenterally with OVA (No detectable anti-LT response) (Student t-test p=0.0323).

7. EXAMPLE 2

Immunization Using HIV-1 Components as Immunogens and mLT as Adjuvant 7.1. Immunization with HIV-1 Viral Lysate A commercially available HIV-1 viral lysate preparation was used an as immunogen in this study (Advanced Biotechnologies, Inc., Columbia Md.). The HIV-1 viral lysate preparation was derived from tissue culture sucrose density purified HIV-1 IIIB inactivated with Triton X-100 and heat. Analysis of this material indicated the presence of the following structural proteins when reacted with HIV-1 positive human sera: p17, p24, p31, gp41, p51, p55, p66, gp120 and gp160.

Figure 6:
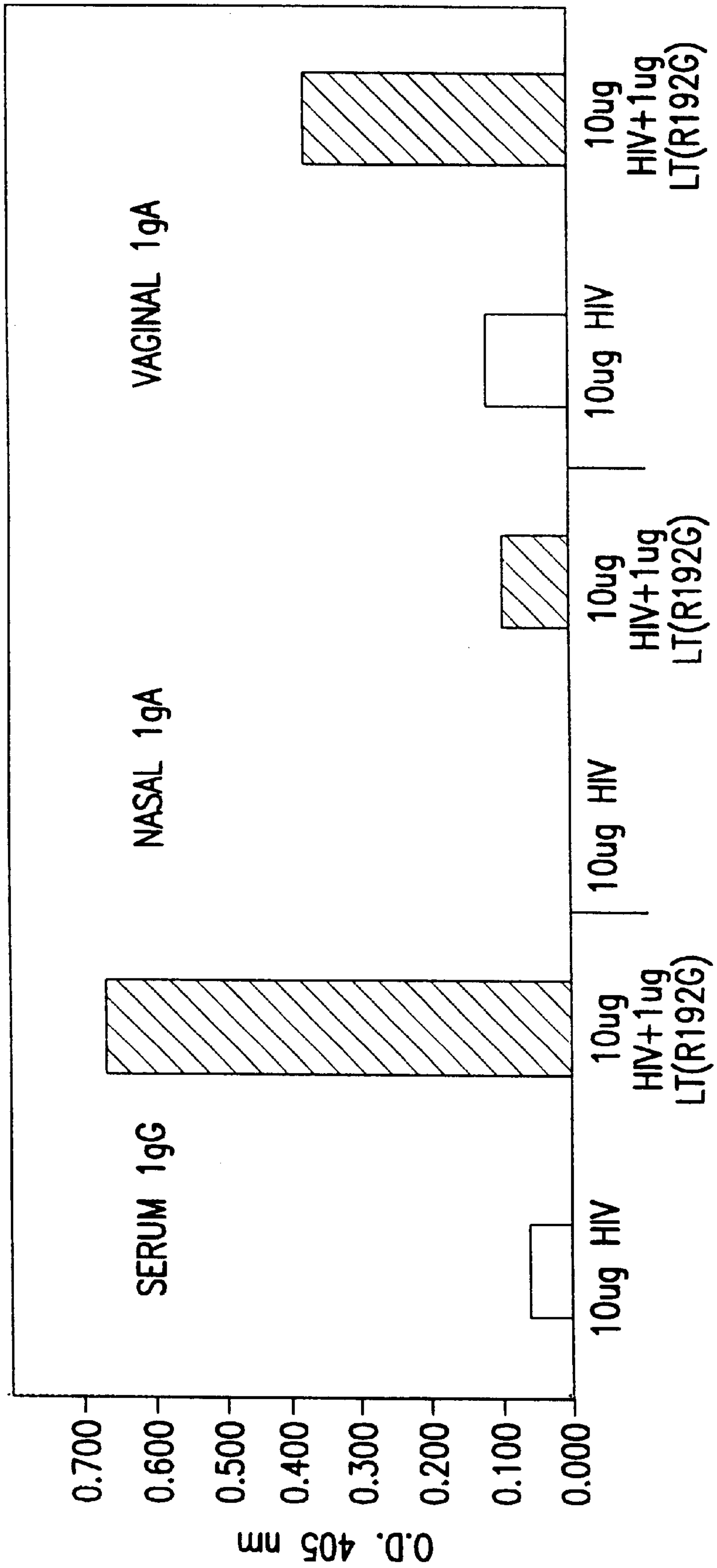
FIG. 6 illustrates anti-HIV serum IgG levels and nasal and vaginal IgA levels of mice immunized intranasally (i.n.) with HIV-1 viral lysate (HIV), either with or without mLT (LT(R192G)). See text of Section 7.1 for details.

Two groups of BALB/c mice were immunized i.n. with 10 μg HIV-1 viral lysate with or without mLT (LT(R192G)). Animals were immunized four times without a parenteral boost and humoral anti-HIV responses were analyzed. Individual serum, nasal and vaginal samples were examined by ELISA for antibodies directed against the viral lysate. Serum samples were diluted 1:8 and vaginal and nasal washes were diluted 1:2 for ELISA analysis. The procedure used to collect vaginal secretions results in the dilution of vaginal secretions by a factor of 10 [Staats et al., 1996, J. Immunol. 157:462–472]. Thus, antibody titers in undiluted vaginal secretions are approximately 10-fold higher than shown. Results are illustrated in FIG. 6. Values reported are the mean OD 405 nm for each group of animals.

The results presented in FIG. 6 show that animals immunized i.n. with the HIV-1 viral lysate in conjunction with mLT (LT(R192G)) had significantly higher anti-HIV serum IgG, nasal and vaginal IgA antibody titers than did animals immunized i.n. with HIV-1 viral lysate alone. These findings are clearly important because they demonstrate the utility of mLT as an adjuvant with HIV for development of both serum and mucosal antibody responses.

7.2. Immunization with HIV-1 gp120

The HIV-1 envelope glycoprotein gp120 has been the subject of numerous vaccine studies in non-human primates and humans. Immunization with gp120, either in combination with various adjuvants or as expressed by live attenuated viral or bacterial vectors, induces anti-retroviral CD4 T-cell proliferative responses, anti-retroviral CD8 cytotoxic lymphocytes (CTLs), and antibodies capable of neutralizing laboratory adapted retrovirus strains [Haynes, 1996, Lancet 348:933–937]. However, Sullivan et al. [1995, J. Virol. 69:4413–4422] have recently shown that anti-recombinant gp120 antibodies raised in animals or in human volunteers neutralize HIV grown in laboratory adapted T-cell lines but not in primary isolates of the virus grown in peripheral blood mononuclear cells (PBMCs). These findings, coupled with the observation of Kahn et al. [J. Infect. Dis. 171:1343–1347] demonstrating that parenteral immunization with gp120 did not protect against HIV-1 infection require that other immunization strategies be explored.

For these studies, groups of BALB/C mice were immunized with a commercially available HIV-1 recombinant gp120 preparation (Advanced Biotechnologies, Inc., Columbia Md.). Mice were immunized i.n. or subcutaneously (s.c.) with 1 μg HIV-1 gp120 with or without mLT (LT(R192G)). Animals were immunized i.n. or s.c. three times with or without an i.p. boost and their humoral and cellular anti-gp120 responses analyzed.

Pooled serum and vaginal samples were examined by ELISA for antibodies directed against gp120. Serum samples were diluted 1:8 and vaginal washes diluted 1:2 for ELISA analysis. Values reported are OD 405 nm multiplied by the appropriate dilution factor. The procedure used to collect vaginal secretions results in the dilution of vaginal secretions by a factor of 10 [Staats et al., 1996, J. Immunol. 157:462–472]. Thus, antibody titers in undiluted vaginal secretions are approximately 10-fold higher than shown. Results are presented in FIGS. 7 and 8. Mononuclear cells from the spleens of immunized animals were analyzed for cytokine production in antigen restimulation assays. Results are presented in FIG. 9.

Figure 7:
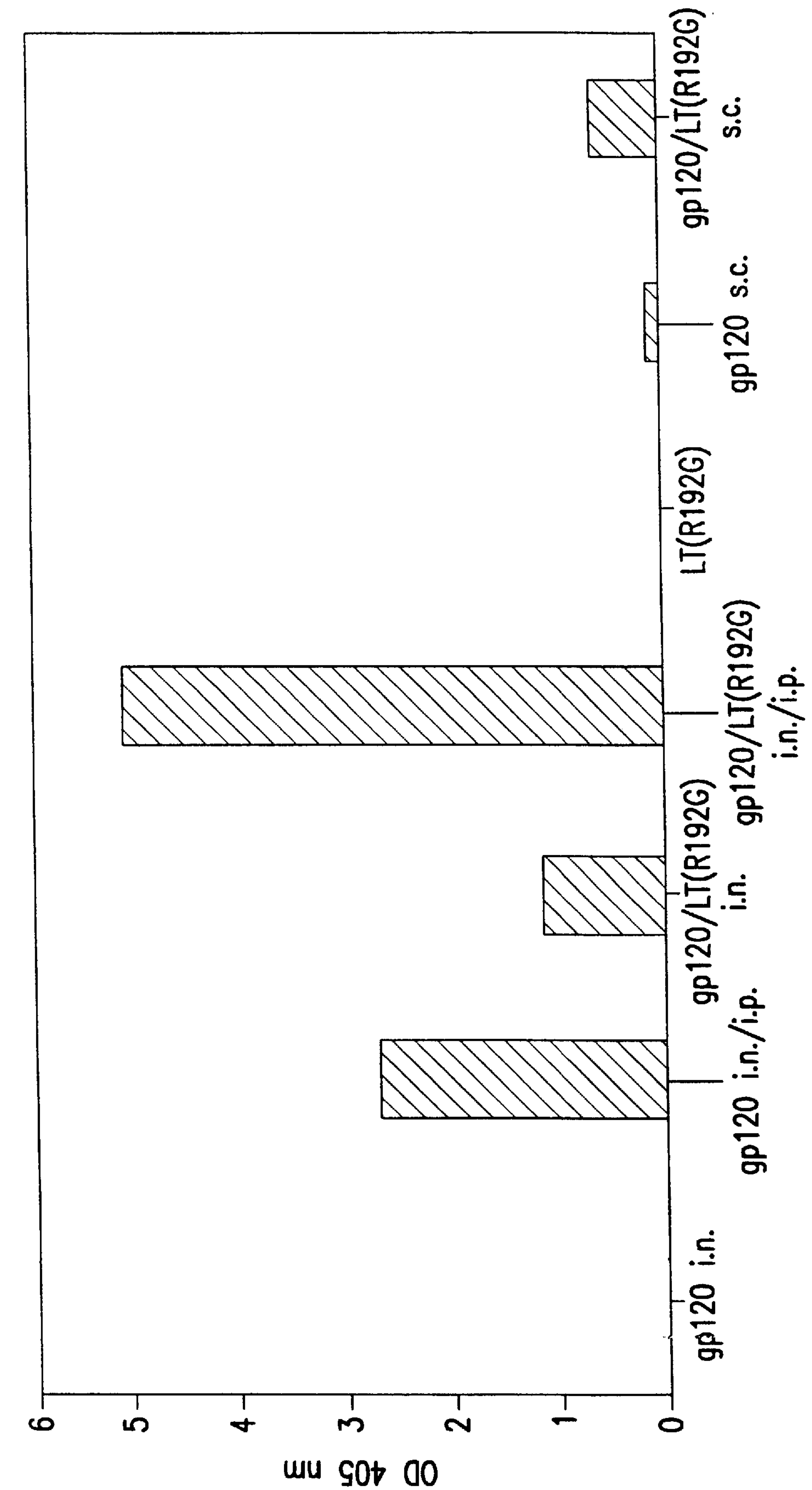
FIG. 7 illustrates anti-gp120 serum IgG levels of mice immunized intranasally (i.n.) or subcutaneously (s.c.) with gp120 with or without mLT (LT(R192G)), and with or without an intraperitoneal (i.p.) boost. See text of Section 7.2 for details.

FIG. 7 shows that animals immunized i.n. or s.c. with gp120 in conjunction with mLT (LT(R192G)) had significantly higher anti-gp120 serum IgG antibody titers than did animals immunized i.n. with gp120 alone.

Figure 8:
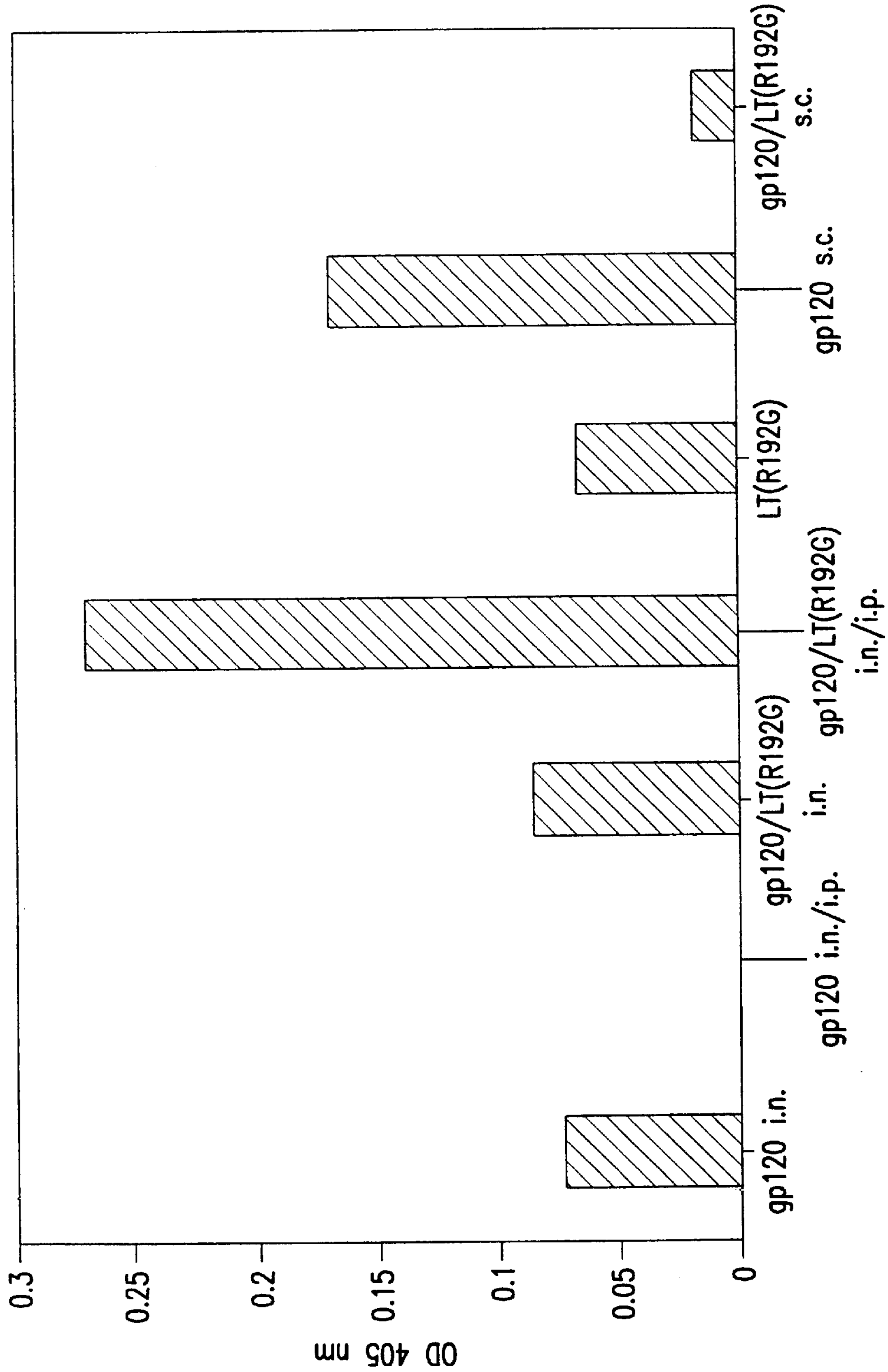
FIG. 8 illustrates anti-gp120 vaginal IgA levels of mice immunized intranasally (i.n.) or subcutaneously (s.c.) with gp102 with or without mLT (LT(R192G)), and with or without an i.p. boost. See text of Section 7.2 for details.

FIG. 8 shows that the highest vaginal anti-gp120 IgA responses were observed in animals immunized i.n. with gp120 in conjunction with mLT and boosted i.p. with gp120.

These results show clearly that the magnitude and distribution of the anti-gp120 antibody response can be influenced by the route of immunization, use of mLT as an adjuvant, and parenteral boosting following mucosal priming.

Figure 9:
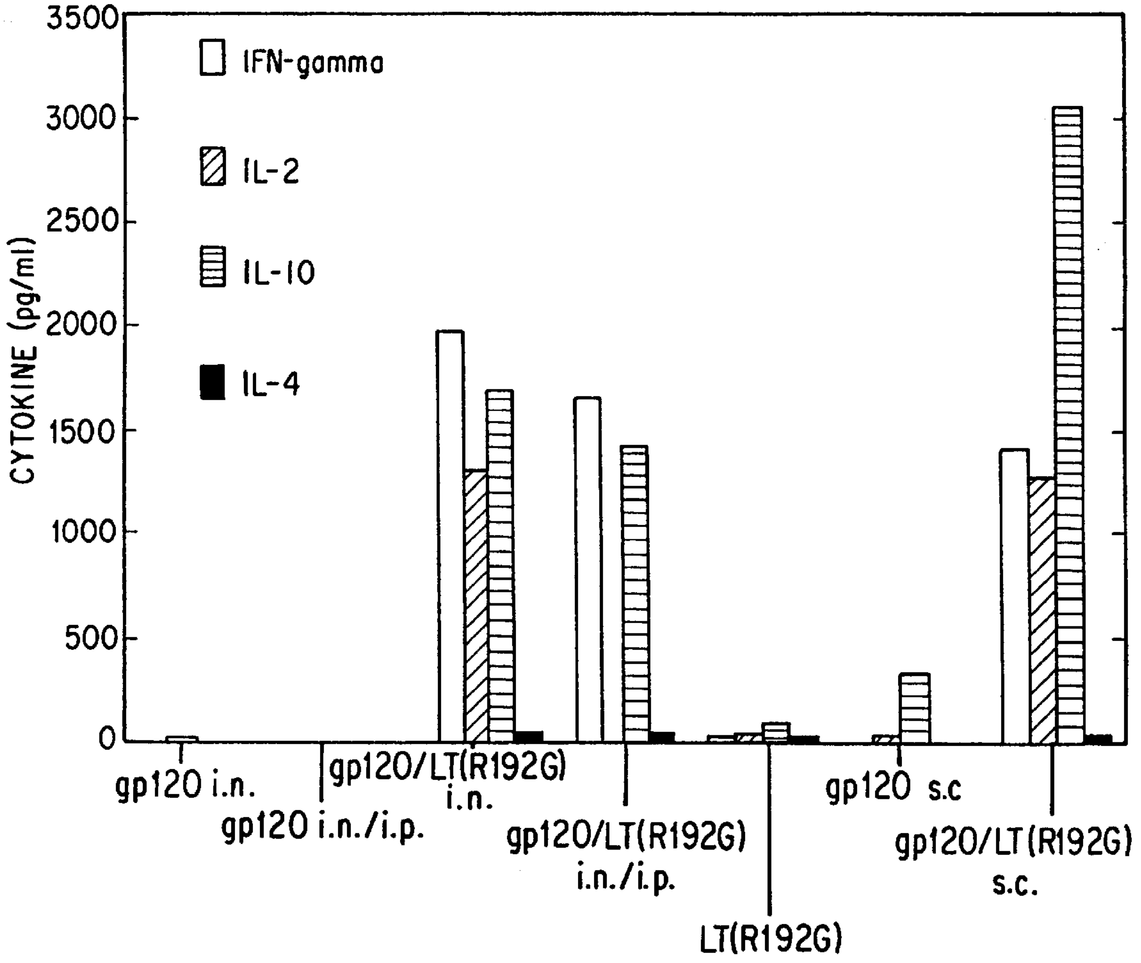
FIG. 9 shows levels of the cytokines IFN-γ, IL-2, IL-10, and IL-4 expressed by spleen mononuclear cells from mice immunized intranasally (i.n.) or subcutaneously (s.c.) with gp120 with or without mLT (LT(R192G)), and with or without an i.p. boost. See text of Section 7.2 for details.

FIG. 9 shows that there was a limited cytokine response by spleen mononuclear cells from animals immunized i.n. or s.c. with gp120 alone. By contrast, mononuclear cells from animals immunized i.n. or s.c. with gp120 in conjunction with mLT had significantly increased production of antigen-specific IFN-γ, IL-2, and IL-10.

These findings are significant because they demonstrate that both humoral and cellular anti-gp120 responses are elicited by immunization with gp120 in conjunction with mLT, which can greatly facilitate the induction of both $T_H1$ and $T_H2$ antigen-specific cytokine responses. Moreover, the qualitative and quantitative aspects of both the humoral and cellular response are determined by the use of mLT as an adjuvant. The route of immunization may also be important. Parenteral boosting following mucosal priming may be advantageous.

8. DEPOSIT OF MICROORGANISMS

The following plasmid was deposited with the American Type Culture Collection (ATCC), 10801 University Boulevard, Manassas, Va. 20110-2209 on Aug. 18, 1994; and has been assigned the indicated accession number:

| Plasmid | Accession Number |
|---|---|
| pBD95 in *E. coli* LTR 192G | ATCC 69683 |

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

It is also to be understood that all base pair and amino acid residue numbers and sizes given for nucleotides and peptides are approximate and are used for purposes of description.

A number of references are cited herein, the entire disclosures of which are incorporated herein, in their entirety, by reference.

What is claimed is:

1. A method of inducing both humoral and cellular immune responses to an HIV virus in a mammalian host, comprising administering an effective amount of an HIV antigen and an effective amount of an adjuvant comprising a mutant *E. coli* heat-labile enterotoxin holotoxin, in which arginine at amino acid position 192 is replaced with glycine, which holotoxin in substantially less toxic than native *E. coli* heat-labile enterotoxin holotoxin as measured in the Y-1 adrenal cell assay and which has immunologic adjuvant activity but lacks adenosine-di-phosphate (ADP) ribosylating enzymatic activity as measured by the nicotinamide-adenine-dinucleotide (NAD) Agmatine ADP-ribosyltransferase assay.

2. The method of claim 1 wherein the HIV antigen and the mutant enterotoxin holotoxin is administered mucosally.

3. The method of claim 1 wherein the HIV antigen and the mutant enterotoxin holotoxin are in an acceptable pharmaceutical carrier.

4. The method of claim 1 wherein a serum antibody response is produced.

5. The method of claim 1 wherein a mucosal antibody response is produced.

6. The method of claim 1 further comprising administering a subsequent boost of an HIV antigen alone or in combination with an adjuvant which is a mutant *E. coli* heat labile enterotoxin holotoxin in which arginine at amino acid position 192 is replaced with glycine.

7. The method of claim 1 wherein the HIV antigen and the mutant enterotoxin holotoxin comprise an admixture delivered in a single dose.

8. The method of claim 7 wherein the admixture is administered by a route of administration selected from the group consisting of intradermal, intramuscular, intraperitoneal, intravenous, subcutaneous, transdermal, epidural, pulmonary, oral, nasal, gastric, intestinal, rectal, vaginal, and urethral routes.

9. The method of claim 1 wherein the HIV antigen is an HIV lysate.

10. The method of claim 1 wherein the HIV antigen is a gp120 glycoprotein.

11. The method of claim 1 wherein the HIV antigen and the holotoxin are administered simultaneously.

12. The method of claim 1 wherein the HIV antigen and the holotoxin are administered separately within a short time of each other.

13. The method of claim 1 wherein the HIV antigen is administered by a route of administration selected from the group consisting of intradermal, intramuscular, intraperitoneal, intravenous, subcutaneous, transdermal, epidural, pulmonary, oral, nasal, gastric, intestinal, rectal, vaginal, and urethral routes.

14. The method of claim 1 wherein the holotoxin is administered by a route of administration selected from the group consisting of intradermal, intramuscular, intraperitoneal, intravenous, subcutaneous, transdermal, epidural, pulmonary, oral, nasal, gastric, intestinal, rectal, vaginal, and urethral routes.

* * * * *